United States Patent
Ehlke et al.

(10) Patent No.: US 8,463,741 B2
(45) Date of Patent: Jun. 11, 2013

(54) DIGITAL PATHOLOGY SYSTEM

(75) Inventors: Joshua Todd Ehlke, Dallas, TX (US); Narasimha Rao Khandavilli, Pittsburgh, PA (US); Timothy Mark McVaugh, Mars, PA (US); Anthony J. Melanson, Pittsburgh, PA (US); Steve Selzer, Pittsburgh, PA (US); Curtis Stratman, Pittsburgh, PA (US); Marina Virnik, New York, NY (US); Joshua Micah Weihnacht, Brooklyn, NY (US); Zhen Zeng, San Francisco, CA (US)

(73) Assignee: Omnyx, LLC, Pittsburgh, PA (US)

( * ) Notice: Subject to any disclaimer, the term of this patent is extended or adjusted under 35 U.S.C. 154(b) by 239 days.

(21) Appl. No.: 12/554,276

(22) Filed: Sep. 4, 2009

(65) Prior Publication Data

US 2011/0060766 A1    Mar. 10, 2011

(51) Int. Cl.
*G06F 17/30* (2006.01)

(52) U.S. Cl.
USPC .................................. 707/608; 705/2; 705/3

(58) Field of Classification Search
USPC ............. 382/240, 151, 128; 378/37; 707/802, 707/10, 661
See application file for complete search history.

(56) References Cited

U.S. PATENT DOCUMENTS

| | | | |
|---|---|---|---|
| 5,793,969 A | 8/1998 | Kamentsky et al. | |
| 5,924,074 A * | 7/1999 | Evans | 705/3 |
| 6,272,235 B1 | 8/2001 | Bacus et al. | |
| 6,396,941 B1 | 5/2002 | Bacus et al. | |
| 6,466,690 B2 | 10/2002 | Bacus et al. | |
| 6,522,774 B1 | 2/2003 | Bacus et al. | |
| 6,652,456 B2 * | 11/2003 | Gelfand et al. | 600/300 |
| 6,674,881 B2 | 1/2004 | Bacus et al. | |
| 6,711,283 B1 | 3/2004 | Soenksen | |
| 6,785,410 B2 * | 8/2004 | Vining et al. | 382/128 |
| 6,904,161 B1 | 6/2005 | Becker et al. | |
| 6,917,696 B2 | 7/2005 | Soenksen | |
| 7,133,543 B2 * | 11/2006 | Verwoerd et al. | 382/128 |
| 7,194,709 B2 * | 3/2007 | Brankner | 382/151 |
| 7,292,251 B1 | 11/2007 | Gu et al. | |
| 7,359,548 B2 | 4/2008 | Douglass et al. | |
| 7,406,150 B2 * | 7/2008 | Minyard et al. | 378/37 |
| 7,457,446 B2 | 11/2008 | Soenksen | |
| 7,474,795 B2 * | 1/2009 | Sirohey et al. | 382/240 |
| 7,490,085 B2 * | 2/2009 | Walker et al. | 1/1 |
| 7,518,652 B2 | 4/2009 | Olson et al. | |
| 7,587,368 B2 * | 9/2009 | Felsher | 705/65 |
| 7,756,309 B2 * | 7/2010 | Gholap et al. | 382/128 |
| 8,117,549 B2 * | 2/2012 | Reiner | 715/751 |
| 2003/0163031 A1 | 8/2003 | Madden et al. | |
| 2004/0004614 A1 | 1/2004 | Bacus et al. | |
| 2005/0033657 A1 | 2/2005 | Herrington et al. | |

(Continued)

*Primary Examiner* — James Trujillo
*Assistant Examiner* — Thong Vu
(74) *Attorney, Agent, or Firm* — Duane Morris LLP

(57) ABSTRACT

A digital pathology system has a central workflow server hosting digital pathology application services and supporting one or more pathology workstations. The digital pathology system may include one or more image servers, providing digital images of sample specimen slides that are associated with medical cases. Residing at and executing on each pathology workstation is a digital pathology application client, which is the counterpart of digital pathology application services at the central workflow server. The combination of digital pathology application services at the central workflow server and digital pathology application client at each pathology workstation support a pathology workflow software module and a slide viewer software module. The present disclosure also describes a method of operation and/or use of the digital pathology system.

40 Claims, 34 Drawing Sheets

U.S. PATENT DOCUMENTS

| | | |
|---|---|---|
| 2007/0066875 A1* | 3/2007 | Horn et al. .................... 600/300 |
| 2007/0081699 A1* | 4/2007 | Avinash et al. ............... 382/128 |
| 2007/0136095 A1* | 6/2007 | Weinstein ......................... 705/2 |
| 2007/0140543 A1 | 6/2007 | D'Errico et al. |
| 2007/0141711 A1* | 6/2007 | Stephens et al. ................ 436/43 |
| 2008/0273788 A1 | 11/2008 | Soenksen et al. |
| 2008/0279439 A1* | 11/2008 | Minyard et al. ............... 382/131 |
| 2009/0204897 A1 | 8/2009 | Sogge et al. |
| 2009/0222746 A1* | 9/2009 | Chirica et al. ................ 715/762 |
| 2009/0254572 A1* | 10/2009 | Redlich et al. .................. 707/10 |
| 2009/0316977 A1* | 12/2009 | Juncker et al. ................ 382/133 |
| 2010/0250497 A1* | 9/2010 | Redlich et al. ................ 707/661 |
| 2011/0270123 A1* | 11/2011 | Reiner ......................... 600/558 |

* cited by examiner

PAST CASE FINAL REPORT 1200

PUSHBUTTON 1210

| SY12-1274 | | | 05/04/08 |
|---|---|---|---|
| SY12-1274 | Signed Out Patient Robinson, Mark | Clinician Dr. Colleen Grose | MRN # 45-6789 |

Final Report | Case Information | Requisition Sheet

Final Diagnosis

Part 1: URINARY BLADDER, RIGHT LATERAL WALL, CYSTOSCOPIC BIOPSY

1. PARTIALLY DENUDED UROTHELIUM WITH NO SIGNIFICANT ABNORMALITY
2. NO EVIDENCE OF IN-SITU OR INVASIVE NEOPLASIA
3. DETRUSOR MUSCLE IS PRESENT IN THIS BIOPSY

Part 2: URINARY BLADDER, DOME, CYSTOSCOPIC BIOPSY

1. BENINGN UROTHELIUM WITH MILD CHRONIC CYSTITIS
2. NO EVIDENCE OF IN-SITU OR INVASIVE NEOPLASIA
3. DETRUSOR MUSCLE IS PRESENT IN THIS BIOPSY

Comment:
Part 1:

The biopsy shows high-grade papillary carcinoma. The biopsy is very superficial, with a minimal amount of lamina propia, and no detrussor muscle. It is therefore not possible to assess invation on this material.

The carcinoma shows weak positive immunostaining for CK7 and negative immunostaining for prostatic specific antigen (PSA and prostate specific acid phosphatase (PSAP). The immunohistochemical staining pattern supports the urothelial origin of the tumor.

[ ] VIEW SLIDES

Figure 12

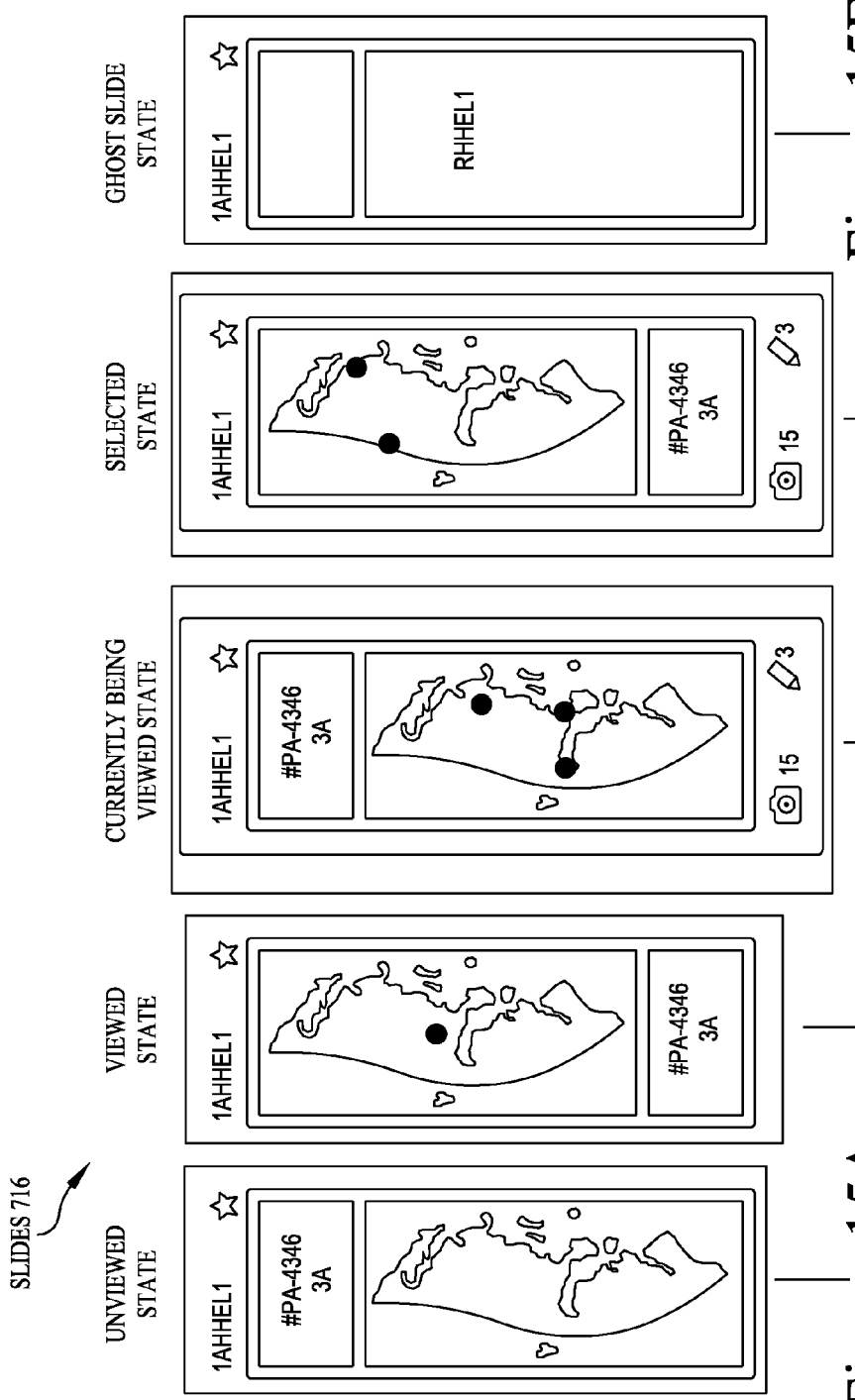

(ACTIVE VIEW)

(INACTIVE VIEW)

DIGITAL PATHOLOGY SYSTEM

BACKGROUND

1. Field of the Disclosure

This disclosure concerns an information system and techniques for processing images and associated data. In particular, an information system for handling microscopic digital images of pathology and histology samples and the like organizes and manages pathologists' workflow using a graphical user interface and visualization mechanisms that are efficiently computerized but resemble the look and feel of working with glass specimen slides, optical microscopes and patient paperwork files.

2. Related Art

Pathology is the study and diagnosis of disease through examination of organs, tissues, bodily fluids and even whole bodies (autopsies). Typically, tissue samples are taken, prepared and examined under magnification. Pathologists are physicians who diagnose and characterize disease by examining biopsies, bodily fluid, duct scrapings and similar samples. In a typical operation, tissue samples might be prepared by being sliced. The slices are mounted on glass slides or in the case of a fluid, a slide is smeared. A reagent or stain might be applied by a specialist called a histotechnician to enhance visible contrast. The sample is covered with a cover slip or cover glass. The slide is typically labeled as to sample identity, and may be associated with other slides for the same patient as well as with a patient file containing other information such as patient history information and test results. When the pathologist takes up the file, he or she reviews the available information, places the slide in a microscope, adjusts for selected viewing position, magnification, focus, etc., and examines the sample. The pathologist might take notes, make a diagnosis, call for other tests or otherwise take action.

Different pathologists may have their personal techniques, but their work has changed very little for decades. Each job unit, for example, may be a medical "case," which is usually a single instance of a patient with a primary medical concern, has a unique file or case number. Associated with each case may be one or more specimens, which are the samples removed from the patient. The slides are standard sized glass rectangles used to hold stained tissue under a cover slip. Each slide associated with a case likewise has a unique slide number. A case may include multiple slides. The slides are usually kept in a slide tray that may have multiple slots for holding multiple slides, from which the slides are taken for viewing.

Slide trays have typically been carried around with accompanying paperwork, which might represent just part of the information associated with the patient's complete file. From the pathologist's standpoint, slide trays and accompanying paperwork are referred to as case "packages." The case packages can be a means by which work is distributed to pathologists, for example with responsibility to attempt a diagnosis being assigned to a pathologist together with handing over custody of a case package. A pathologist knows which cases he/she is working on, and can judge workload, by the stack of case packages at his/her workstation.

A pathologists might further organize their case packages into physical piles according to categories that are meaningful to the pathologist, such as the status of the case packages in a sequence of operations, or their priority or urgency or by another category. Thus, for example, the workload could be found in several piles that include but are not limited to a "currently reviewing" pile; a "complete but not yet filed away" pile; a "signed out but waiting for follow up stains" pile; an "incomplete" pile, which may be a pile that is waiting for more slides and/or paperwork to be received; a "need to review again" pile, which may be a pile that may set aside for some reason such as to review with a trainee or other pathologist; an "educational" pile, which may be a pile that is set aside as an exemplar and possibly the subject of a conference and/or future educational reference; and the like.

Although case packages are discrete physical items that can be treated as units of workload, there are drawbacks associated with the need to handle the packages and their contents manually. For example, the physical handling and distribution of case packages may be inefficient and error prone. The physical nature of the slides and paperwork may result, for example, in breakage or misplacement of slides, "lost" case packages or package contents, a risk of mixing the contents of two or more case packages, inability to quickly find or assess the status of cases and so on. The process is characterized by many of the problems associated with manually kept files, with the additional complication of having associated slides. Manual tracking and reporting mechanisms on paper are inefficient to manage, store and monitor. It is difficult to exchange information between interested parties, difficult to archive and quickly retrieve information, and documentation or slides can become missing or misplaced. These problems reduce the pathologists' efficiency and may adversely affect patients waiting for diagnoses. Improved systems and/or processes are needed that are free of the physical constraints and manual nature of current pathology processes, that preferably provide improved reporting and mechanisms for easy and accurate data exchange, information retrieval and information processing.

There is an emerging movement toward digital encoding of microscope imaging data for use in pathology. In a technique called "whole slide imaging" the entire field of view of samples on slides is digitally imaged up to full magnification, providing a set of image file that can be selected and viewed on a computer. The opportunity for whole slide imaging to take pathology into the digital realm is enticing because after the sample has been imaged (namely after all possible views of the sample have been encoded digitally), the process can be made free of the ubiquitous glass slides. Among other benefits, whole slide imaging eliminates the burden of moving and storage of physical glass slides, permits pathologists to process cases when they are away from the slides and away from a microscope, reduces the risk of losing or mixing up patient slides and giving the wrong diagnosis to a patient, reduces the work of pathology assistants who attend to slides that come to a case package late, and may provide opportunities for computer vision algorithms to help pathologists identify specific features in the images they are viewing.

Despite the potential advantages, current digital slide viewer technology has not been widely accepted into day-to-day practice. Technical issues remain to be overcome, such as obtaining repeatably consistent image quality, dealing with the large number of image files associated with every slide, providing adequate hardware and/or software at reasonable expense to maintain image quality and processing speed and similar issues. Therefore, what is needed are digital pathology systems and/or processes that provide improved performance for processing and viewing digital images of slides.

SUMMARY OF THE DISCLOSURE

According to an aspect of the present disclosure, the automated handling of digital pathology images, and also the speed and efficiency of such handling, are facilitated in part by addressing technical and also human issues associated with handling case package information. Pathologists are proficient with operating microscopes and have experience in dealing with case packages as discrete workload units. What is needed is a digital pathology system and/or process that provides an image viewing and case management experience that substantially resembles or even emulates the slide navigation tools and features that are familiar to pathologists who have experience using microscopes and traditional case package handling techniques. For example, pathologists' workflow organization comes from sorting and categorizing case packages, and their speed and efficiency with microscopes is due in part from an acquired ability to navigate slides without taking their eyes off the microscope image. An object of the present disclosure, therefore, is to provide digital pathology systems and/or processes that use some of the same skills, facilitating smooth transition from physical case package piles and queues to the benefits of digital pathology systems, digital images and networked data, and in all respects so serve the overall efficiency and effectiveness of pathologists at work.

In one embodiment, a central workflow server hosts digital pathology application services for supporting one or more pathology workstations. The workflow server is connected to the pathology workstations via a network. The workflow server is in at least intermittent data communication with one or more image servers, which are the source of digital images of the slides that are associated with medical cases. The workflow server also includes a database for storing case data and any other information related to the digital pathology system, such as image catalog information for identifying the image server that is the source of the digital slide images of any medical case of interest, and furthermore can serve as a portal to a larger medical information database containing patient information beyond the particular case that brought the attention of the pathologist.

Residing at and executing on each pathology workstation is a digital pathology application client, which is the counterpart of digital pathology application services at the central workflow server. The combination of digital pathology application services at the central workflow server and digital pathology application client at each pathology workstation support a pathology workflow software module and a slide viewer software module.

The pathology workflow module supports workflow and case management, including a work list and detailed case information. The pathology workflow module supports the activities that pathologists might previously have performed with physical case packages, including categorizing, sorting and organizing their work and finding information about cases. Associated with the pathology workflow module is set of workflow visualization elements (e.g., workflow menus) by which pathologists may view the list of cases to which they have been assigned, select one or more cases of interest, select one or more slides of any selected cases, and process the detailed information of the selected cases and/or slides. In one example, the workflow menus of the pathology workflow module are presented to pathologists on a first computer display area of pathology workstation that is dedicated to the presentation of workflow menus only. A distinct display or display area associated with a viewer module is used for viewing the magnified sample images.

The viewer module supports the activities that pathologists currently perform with a microscope and slide tray, including selecting or moving among viewing points and magnifications, viewing images, making annotations that become associated with a particular location on a slide, etc. Associated with the viewer module is a set of viewer visualization elements (e.g., viewer menus) by which pathologists may view, navigate, and manipulate the digital images of any slides of any cases selected via the workflow menus. Advantageously, the viewer menus provide visualization elements with one or more characteristics that resemble the slide navigation tools and features that are familiar to pathologists who have experience using microscopes and physical slides as opposed to image data files. In one example, the viewer menus of the viewer module are presented to pathologists on a second computer display of pathology workstation that is dedicated to viewer menus and viewing functions only.

An advantageous aspect of the digital pathology system and associated methods according to the present disclosure is that the combination of workflow menus and viewer menus provides a hierarchy of visual elements that appear to the pathologist and are used by the pathologist in a way that substantially resembles over even mimics corresponding features and elements that are known to the pathologist from using prior art physical pathology case packages and microscope instrumentation.

By providing workflow features including user interface display indicia and user operated controls for workflow and imaging, which resemble and/or mimic the slide handling, image navigation, information handling and other tools and features that are familiar to pathologists who have experience with prior art microscope systems, the change to digital imaging and network data communications not only exploits the benefits of modern computing but also benefits by exploiting the skill and expertise that the pathologist has developed by using manual microscope systems.

The digital pathology system and associated methods of the present disclosure are made efficient with respect to data communications requirements for network data communications. Bandwidth requirements are minimized by transmitting image data files only as to portions of a digital slide image that are being viewed or are adjacent to an image being viewed and might be viewed next by adjustment of microscopic magnification or stage position, i.e., system supports just-in-time viewing. In this way, the network data bandwidth requirements and performance of the system are optimized.

The disclosed system and associated methods provide the capability to view multiple cases and/or slides simultaneously. Further, multiple images can be processed from a single slide.

One object of the digital pathology system and associated methods is to improve the overall efficiency, accuracy and effectiveness of pathologists. Another object is to overcome the physical constraints and comparative clumsiness of manual prior art pathology systems and methods that rely on handling paper files, glass slides and racks for holding the slides, while retaining benefits derived from user familiarity with these physical items.

Another object of the disclosed system and methods is to facilitate a smooth transition for pathologists and their organizations and workplaces, from physical microscope systems to digital pathology systems.

As additional benefits, the disclosed digital pathology system and methods facilitate and improve reporting processes and data handling. The system and methods provide mechanisms for easy data exchange and retrieval. The system is readily scalable as well as capable of integration into patient medical information databases, institutional or organizational data processing systems.

The foregoing advantages, benefits and aspects are provided by a data processing system for handling images of specimens and associated data, with a source of digital image data representing images of the specimens to a predetermined magnification, an image database containing memory for storing the digital image data and associated data relating to the image data, a workflow database containing memory for storing case management data associated with the specimens and a computer workstation comprising at least one digital processor coupled to the image database and to the workflow database. The processor is operable under control of a user to obtain and display selected ones of the images for review, to accept user input and to record in at least one of the image database and the workflow database information resulting from the user input. The processor is programmed to present the image data to the user on a display controlled according to the user input to emulate controls of an optical microscope.

The system and its operation embody a method or process for digitally managing examination of patient samples by a pathologist or technician user. Tissue samples are obtained and prepared on slides that are scanned for digitally encoding microscopic images of at least a predetermined area of the slides encompassing the tissue samples. The images for at least one of a patient, a case, a patient part and a block, are stored as digital data files representing the microscopic images in at least one database, with associated information identifying the images and associated patient medical information.

The images from the slides and the associated patient medical information define a virtual case package containing images and information, and are useful in the manner of physical case packages but without the problems associated with dealing with physical case package paperwork, files, glass slides, slide racks and optical microscopes. Instead, review is facilitated using the virtual case package, namely by providing a workstation having a digital processor in data communication with the at least one database, at least one display and user operated input devices, and operating the digital processor under control of a stored data processing program to present to the user options for selection of case packages and portions of case packages forming a workload, to display the images and information and to record and to store data in the at least one database, data generated as a result of review of the images and information by the user. Presentation and manipulation of the images is controlled by the digital processor to emulate controls of stage positioning and magnification on an optical microscope. Presentation and manipulation of the case packages is controlled by the digital processor and from user input, using icons visually emulating virtual slides and files of a physical case package.

The manipulation or handling encompasses steps that are analogous to the handling of physical slides, in particular, steps in a predetermined sequence for microscopic viewing and at least one of a histological, cytological and pathological study and reporting upon tissue samples associated with patient case files. Each of the patient case files can have images of one or more tissue samples and specimen slides, wherein each said specimen slide corresponds to plural image views in the image database for at least one of diverse locations on the slide and diverse levels of magnification. The images can comprise all viewable locations on the specimens on the slides, up to the predetermined magnification and optionally at lower magnification. Lower magnification images alternatively can be provided by tiling an array of higher magnification images and changing the pixel resolution by image data processing techniques. In any event, the processor is programmed to display to the user a selected location; and wherein the processor is operable for at least one of fetching and processing from the image database, and for displaying to the user, an image at the selected location and level of magnification.

User input can select, navigate, annotate, describe and otherwise deal with images of the specimens, producing information that is stored in the image database. Additionally, case management and workflow information is obtained or generated. The system records, selections by the user in preparation to view the images, status information generated by the digital processor reflecting progress in completion of the steps in the predetermined sequence, and dispositive information entered by the user based on review of the images, for example. The case management information is processed and stored by the digital processor in the workflow database.

The display of images and case management data emulates the content of physical case packages that have files and glass slides, except that case package icons and digital image files are manipulated by the user, for example for categorizing the case packages to define piles, selecting and grouping file icons, selecting among the slides by selecting slide icons, etc. In one example of categorization, slides in the virtual case packages are managed for a reviewed/not-reviewed state, which categorization is indicated by altering at least one of a size, shape, color parameter, orientation and location of the case package icons associated with the slide.

A preferred user workstation is arranged as a pathologist's cockpit. Distinct display areas, that preferably employ two visual monitors, are respectively configured for display of image data, controlled by the user input to emulate the controls of an optical microscope, and for display of the case management information, controlled by at least one of a keyboard and location selecting device. The computer workstation is one of a plurality of workstations coupled over a network to servers maintaining the image database, the workflow database and a medical information database.

BRIEF DESCRIPTION OF THE DRAWINGS

The foregoing aspects, objects and advantages are demonstrated in the following discussion of embodiments, which should be considered exemplary rather than exhaustive or limiting, and refer to the accompanying drawings, wherein:

FIG. 12 shows a view of a past case final report of the workflow main menu of the digital pathology system;

FIGS. 15A through 15E show examples of different states of individual slides shown in the viewer main menu of the digital pathology system;

DETAILED DESCRIPTION

Figure 1:
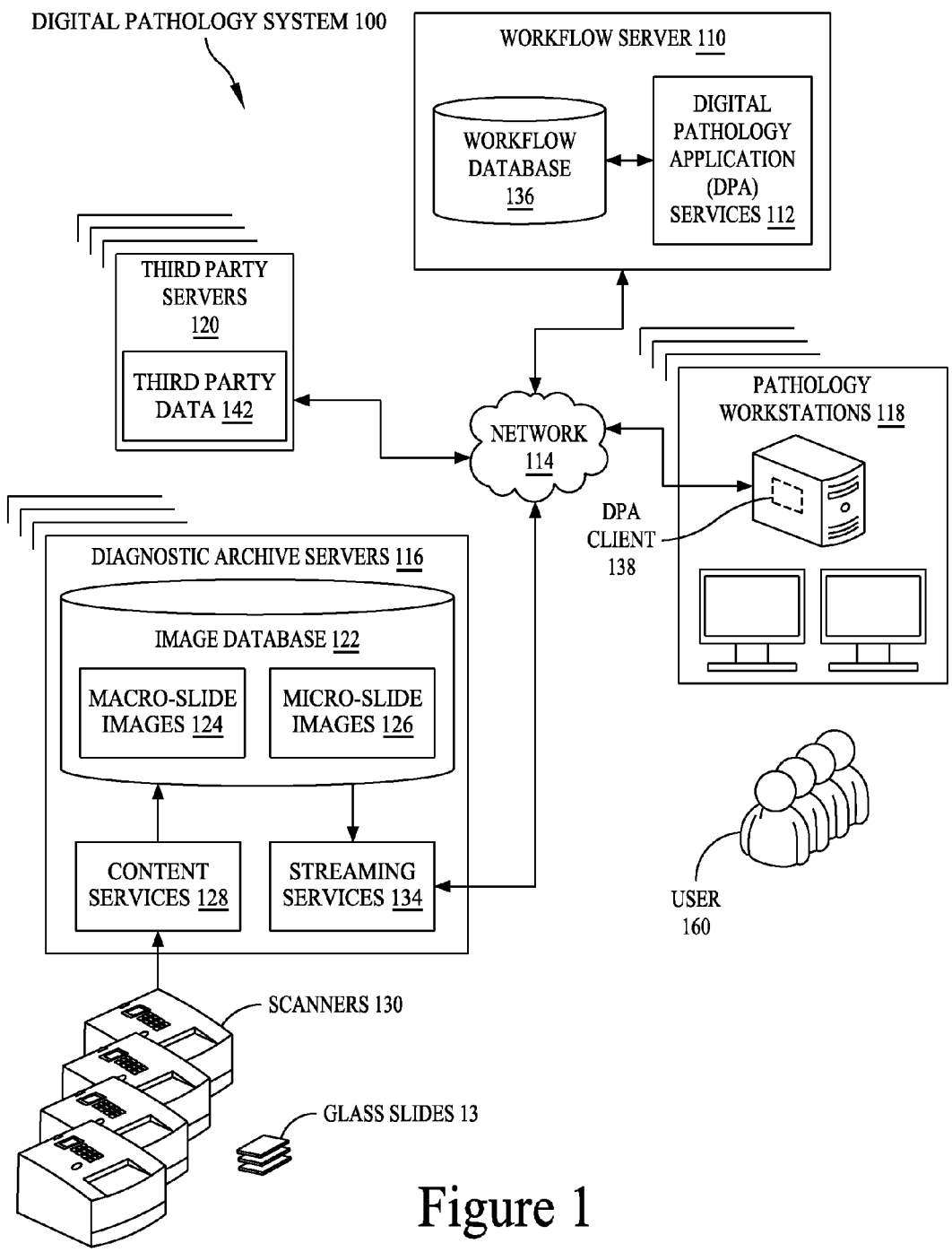
FIG. 1 illustrates functional block diagram of an example of a digital pathology system, according to the present disclosure.

FIG. 1 is a functional block diagram showing an example of a digital pathology system 100 according to the present disclosure. Among other aspects, digital pathology system 100 is configured for manipulation by and interaction with pathologists, and supports graphic visualization elements that resemble the slide navigation tools and features that are familiar to pathologists who have used microscope systems. Such resemblance includes both appearance and function. At the same time, system 100 benefits from the speed, efficiency and computing power of a digital image and data processing system that reduces the need for pathologists to depend upon physical slides, optical microscopes and case package paperwork files.

Digital pathology system 100 may include a workflow server 110, where "workflow" refers primarily to the pathologists' workflow. Workflow server 110 may be a centralized server for hosting digital pathology application (DPA) services 112. Via a network 114, workflow server 110 is in communication with, for example, one or more diagnostic archive servers 116, one or more pathology workstations 118, and one or more third party servers 120 of digital pathology system 100.

Network 114 may be, for example, any local area network (LAN) and/or a wide area network (WAN) for data communication, such as the Internet. Network 114 provides the communication link between any and/or all entities of digital pathology system 100. For example, network 114 provides the communication network by which information may be exchanged between workflow server 110, diagnostic archive servers 116, pathology workstations 118, and/or third party servers 120. Each entity of digital pathology system 100 may have a wired and/or wireless communication interface (not shown) for connecting to network 114.

Diagnostic archive servers 116 are the source of digital images of the slides that are associated with medical cases. Each diagnostic archive server 116 may include an image database 122. Stored on each image database 122 may be a collection of macro-slide images 124 and a collection of micro-slide images 126. Content services 128 manages the inbound flow of scanned slide images. For example, content services 128 of each diagnostic archive server 116 manages the acquisition of macro-slide images 124 and micro-slide images 126 from one or more scanners 130 that are connected to each diagnostic archive server 116. More details of an example of a diagnostic archive server 116 are described with reference to FIG. 3.

Scanners 130 may comprise commercially available slide scanning devices that are suitable for scanning glass slides 132 associated with medical cases. In this way, the images of physical glass slides 132 are digitized and cataloged in a database in association with slide and patient identifying information, and image identifying information such as the image capture magnification, X, Y and optionally Z position on the slide and other such information. In one embodiment, the slide scanners collect a range of images capable of displaying the slide or locations on the slide at a range of magnifications and encompassing any location on the tissue sample or fluid smear that a pathologist may select to view. Streaming services 134 of each diagnostic archive server 116 manages the outbound flow of scanned slide images. For example, streaming services 134 receives and processes requests from any entity logged into or having access to digital pathology system 100 and manages the process of streaming the image data of macro-slide images 124 and/or micro-slide images 126 to the requesting party.

Depending on the capabilities of scanners 130, macro-slide images 124 and/or micro-slide images 126 may be any resolution that is useful in digital pathology system 100. In one example, the scanning resolution of scanners 130 may be in the range of about 0.25 microns/pixel to about 5 microns/pixel (0.25 to 5×10$^{-6}$ m/pixel). Each macro-slide image 124 is a single image that captures the entire slide at low magnification and is useful to determine where the sample resides on the glass slide 132. Each micro-slide image 126 contains an image of a portion only of the whole glass slide 132. In particular, each micro-slide image 126 is an image of a certain area on glass slide 132 that contains tissue. Therefore, multiple micro-slide images 126 are associated with a single glass slide 132. For example, multiple micro-slide images 126 may be stitched together in a tiled fashion to represent a certain glass slide 132 in its entirety. Macro-slide images 124 and micro-slide image 126 are captured using two different types of cameras within scanners 130.

Digital Pathology Application (DPA) services 112 of workflow server 110 provides a centralized application for supporting various functionalities of digital pathology system 100. In one example, DPA services 112 may be used for assigning cases to pathologists, for managing case information and access thereto, for managing access to macro-slide images 124 and/or micro-slide images 126 at diagnostic archive servers 116, for managing user sessions at pathology workstations 118, for supporting reporting mechanisms, for facilitating the exchange of data between any entities of digital pathology system 100, and the like.

Workflow server 110 also includes a workflow database 136 for storing case data and any other information related to digital pathology system 100, such as image catalog information for identifying the diagnostic archive server 116 that is the source of the digital slide images of any medical case of interest. More details of DPA services 112 and workflow database 136 of workflow server 110 are described with reference to FIG. 2.

Residing at and executing on each pathology workstation 118 is a Digital Pathology Application (DPA) client 138, which is the counterpart of DPA services 112 at workflow server 110. DPA client 138 includes a pathology workflow module and a slide viewer module. The pathology workflow module supports workflow and case management, including the work list and detailed case information. It is intended to support the activities that pathologists currently perform with case packages, including sorting and organizing their work and finding information about cases. The viewer module supports the activities that pathologists currently perform with the microscope and slide tray, including viewing images and making annotations. More details of DPA client 138 of each pathology workstation 118 are described with reference to FIG. 4.

Digital pathology system 100 may include one or more third party servers 120 for supplying third party data 142. Third party servers 120 may be associated with any entities, for example sources of medical case information. In one example, a third party server 120 may be a server of an Anatomic Pathology Laboratory Information System (APLIS). APLIS systems support receiving tissue or other samples; histological or other processing of the sample; visual or cytochemical analysis, interpretation, and review of the diagnostic/therapeutic findings; transcription or entry of findings; and a final release by an authorized pathologist or cytotechnologist. In this example, third party data 142 may be medical case information supplied by the APLIS to workflow server 110.

Associated with digital pathology system 100 may be users 160 that are operating pathology workstations 118. In one example, users 160 may be pathologists who have been assigned to medical cases and are using digital pathology system 100 for viewing the digitized images of glass slides 132 and associated information, and are making diagnoses.

Digital pathology system 100 may include any number of diagnostic archive servers 116, any number of pathology workstations 118, and any number of third party servers 120. For this reason, it is advantageous to configure digital pathology system 100 so that it may be easily scaled.

Figure 2:
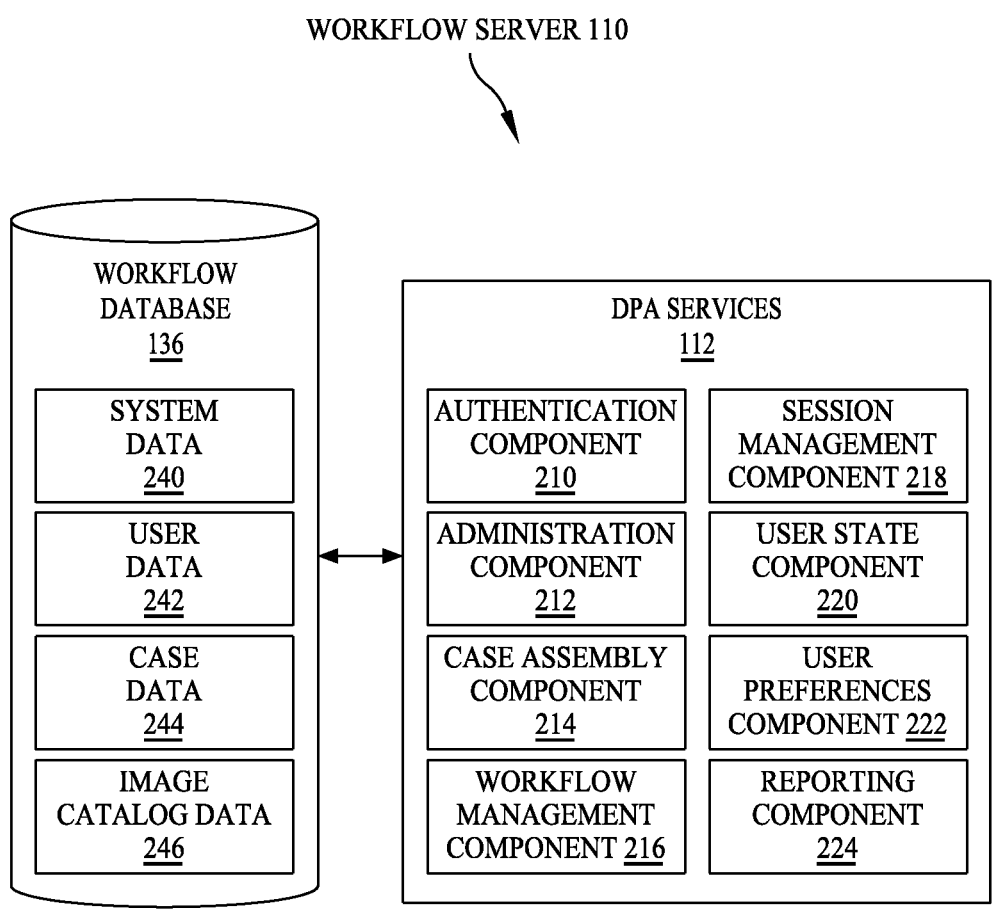
FIG. 2 illustrates functional block diagram of an example of a central workflow server of the digital pathology system.

FIG. 2 is a functional block diagram of an example of workflow server 110 of digital pathology system 100, according to one embodiment. In this example, workflow server 110 includes DPA services 112 and workflow database 136 as described in FIG. 1. However, FIG. 2 shows that DPA services 112 of workflow server 110 may further include, but is not limited to, an authentication component 210, an administrator component 212, a case assembly component 214, a workflow management component 216, a session management component 218, a user state component 220, a user preferences component 222, and a reporting component 224. FIG. 2 also shows that the information stored in workflow database 136 of workflow server 110 may include, but is not limited to, system data 240, user data 242, case data 244, and image catalog data 246.

Authentication component 210 of DPA services 112 may be a software component for authenticating users and controlling data access rights, such as pathologists and/or administrators of digital pathology system 100. For example, authentication component 210 may be used to maintain records of authorized user names, user IDs, user passwords, user locations, name of laboratory associated with each user, and the like, which is accessed during any login attempt of digital pathology system 100. Additionally, authentication component 210 may be used to maintain records of authorized entities of digital pathology system 100 between which information may be exchanged. For example, authentication component 210 may be used to maintain records of authorized diagnostic archive servers 116, pathology workstations 118, and third party servers 120. User and/or entity information that is processed by authentication component 210 may be stored, for example, in system data 240 and/or user data 242 of workflow database 136. Additionally, system data 240 may include, for example, security data, usage data, billing information and the like.

Administrator component 212 of DPA services 112 may be a software component by which administrators (not shown) may add, update, and/or remove authorized users and/or entities of digital pathology system 100. For example, administrator component 212 may be used to process records of users and/or entities of authentication component 210. Further, administrator component 212 may be used by administrators to manage the assignment of medical cases to users 160 (e.g., pathologists) and/or to monitor the status of medical cases that have been assigned.

Case assembly component 214 of DPA services 112 may be a software component by which all information of each medical case is associated. For example, for a certain medical case of a certain patient, case assembly component 214 is used to associate information stored in case data 244 for the certain case to the macro-slide images 124 and/or micro-slide images 126 for the certain case. When a user 160 to which the certain case has been assigned opens the case at his/her pathology workstation 118, case assembly component 214 is used to assemble or otherwise make available information for presentation to the user 160 at his/her pathology workstation 118. The source of case data 244 may be, for example, certain third party data 142 of a certain third party server 120 of digital pathology system 100. In one example, case data 244 may be any digital information about the patient (e.g., medical records), the patient's physician, the slides, the case requisition sheet, tissue parts, assigned pathologist, assigned bench, and so on, that is supplied by an APLIS.

Workflow management component 216 of DPA services 112 is used to initiate a streaming session (viewing session) for a certain user 160 at a certain pathology workstation 118. Workflow management component 216 is used to locate any requested macro-slide images 124 and/or micro-slide images 126 of cases being viewed during any sessions that are active at any pathology workstation 118. For example, workflow management component 216 is used to interrogate image catalog data 246 of workflow database 136 when servicing requests for slide image data. Image catalog data 246 includes records of the locations of macro-slide images 124 and micro-slide images 126 at diagnostic archive servers 116.

Once a user session is initiated, session management component 218 may be used to process requests from pathology workstations 118, process responses to pathology workstations 118, log session data to/from workflow database 136, and the like.

User state component 220 of DPA services 112 may be a software component by which the information of the user's state is saved, such as information about the location on a certain slide that was last viewed by the user. In another example, state component 220 of DPA services 112 may provide the ability for the user to switch between multiple cases while preserving the state of review of each case at the time of the switch. A record is stored of what the user 160 has viewed or viewed last via the workflow menus and viewer menus of digital pathology system 100, so that when the user switches back to the case, review can commence again at the same point without loss of progress. An example of viewing multiple cases simultaneously and preserving the current views at the time of the switch is illustrated with respect to FIGS. 21A and 21B, 22A and 22B, and 23A and 23B.

Once a session is initiated, user preferences component 222 is the software component used to access user data 242 for user preferences information and applies the user preferences to the current session.

Reporting component 224 of DPA services 112 may be a software component by which information that is entered by users 160 and/or processed at pathology workstations 118 may be compiled and integrated into any reporting system and/or format and presented to any interested parties.

Figure 3:
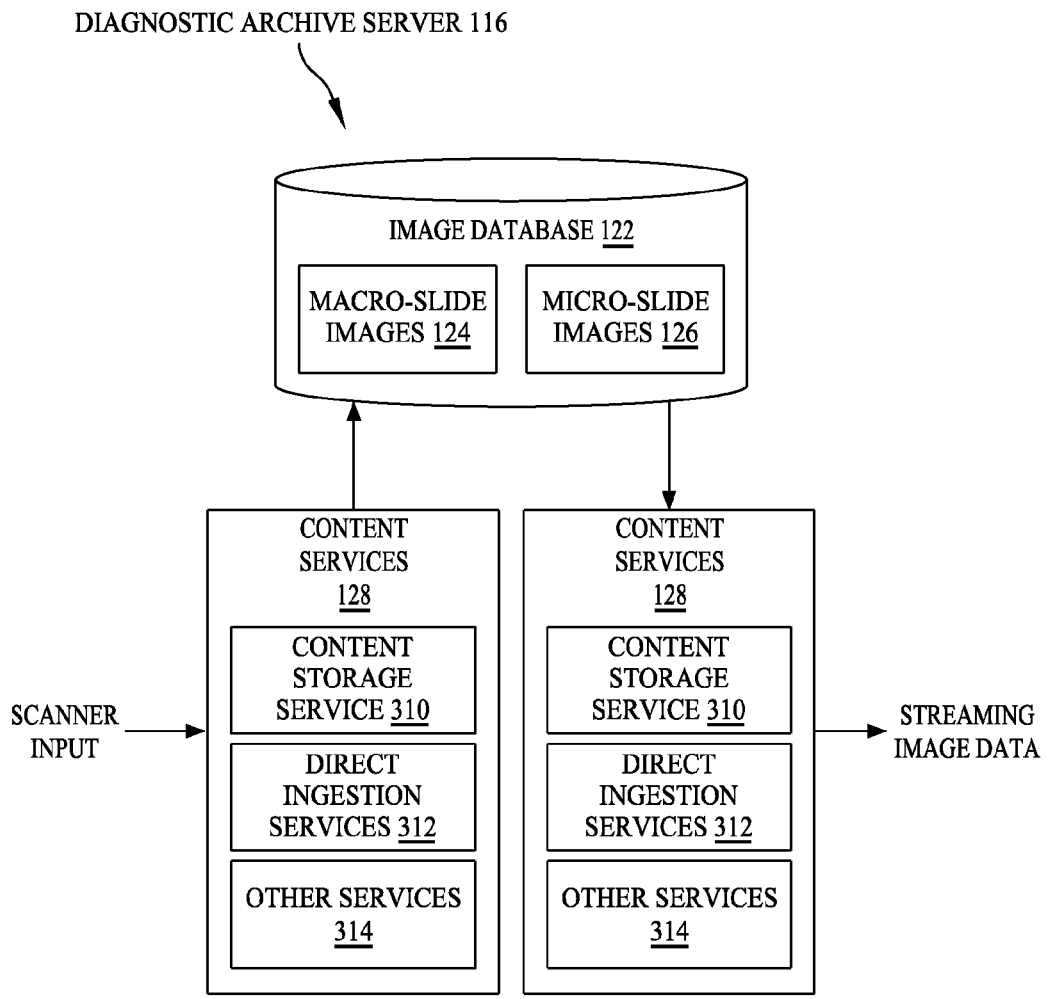
FIG. 3 illustrates functional block diagram of an example of a diagnostic archive server of the digital pathology system.

FIG. 3 is a functional block diagram illustrating an exemplary embodiment of a diagnostic archive server 116 of digital pathology system 100. FIG. 3 shows that diagnostic archive server 116 may include an image database 122 storing macro-slide images 124 and micro-slide images 126, content services 128, and providing image streaming services 134, as described in reference to FIG. 1.

Content services 128 manages the inbound flow of scanned slide images to diagnostic archive server 116. For managing this process, FIG. 3 shows that content services 128 may further include a content storage service 310, direct ingestion services 312, and other services 314.

Content storage service 310 of content services 128 provides a file search function that may be used for locating images within the file system (e.g., NTFS file system) of diagnostic archive server 116. For example, the files may be addressable by using an agreed network path naming convention.

Direct ingestion services 312 of content services 128 manages the acquisition of macro-slide images 124 and micro-slide images 126 from, for example, one or more scanners 130 that may be connected to a certain diagnostic archive server 116. There is metadata associated with each macro-slide image 124 and micro-slide image 126, as is known in connection with image processing systems for slide images.

An example of other services 314 of content services 128 is Image Lifecycle Management (ILM). As pathology cases age, it may be desirable to archive data rather than to maintain the scanned images associated with old cases in an immediately accessible, large, high quality format as might be appropriate for cases that are presently under review. Therefore, other services 314 may include a set of services that are invoked to compress, move, and rename image files based on aging or other attributes of the case to which it belongs. For example, once a case is diagnosed and signed out, the image files can be queued to be compressed or moved to less accessible storage, and thereby to reclaim the memory space that they would otherwise occupy.

Streaming services 134 manages the outbound flow of scanned slide images from diagnostic archive server 116. For managing this process, FIG. 3 shows that streaming services 134 may further include a streaming client 320, a compression engine 322, and a streaming partner 324.

Streaming client 320 of streaming services 134 is software that is used when a pathology workstation 118 is retrieving image data from diagnostic archive server 116 to enable a user 160 to view an image. For example, when a user 160 zooms in on a location in a scanned image, for example changing from 20× to 40× magnification, streaming client 320 may request data to reconstruct the image at a 40× zoom level.

Compression engine 322 of streaming services 134 is responsible for taking relatively large slide image data sets (e.g., uncompressed bitmap macro slide images 124 and/or micro-slide images 126) and compressing them into other file formats, such as the Real-Time Slide (RTS) format or JPEG2000 format. This enables the image data to be efficiently stored in a relatively smaller space and streamed to a pathology workstation 118 using less bandwidth, but also requires processing steps for compression and decompression. Compression engine 322 is responsible for decompression, at either the server or client side, when streaming an image.

Streaming partner 324 of streaming services 134 comprises software that responds to requests to initiate streaming sessions. In other words, when a user 160 requests to view an image through his/her pathology workstation 118, streaming partner 324 is responsible for locating the image from the content services of diagnostic archive server 116 (e.g., via content storage service 310) and beginning a streaming session for that image. Initiating a streaming session creates a token that uniquely identifies the session. The session token is then passed to the requesting party, and all future requests regarding that image include the session token so that streaming partner 324 retains data identifying the image and possibly other information about the session for reference as review of the data progresses.

Figure 4:
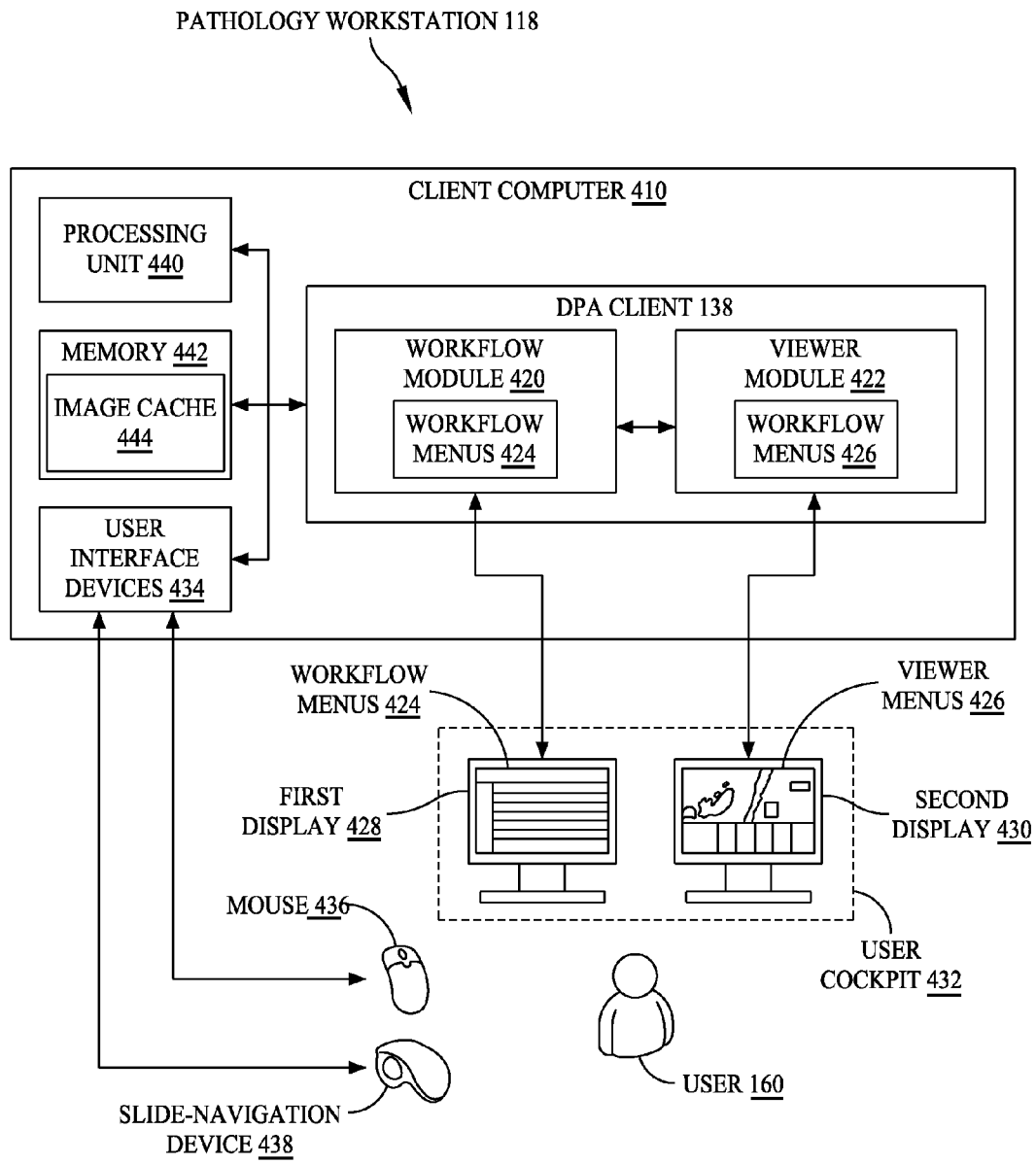
FIG. 4 illustrates functional block diagram of an example of a pathology workstation of the digital pathology system.

FIG. 4 is a functional block diagram illustrating an example of a pathology workstation 118 of digital pathology system 100. A pathology workstation 118 may include, for example, a client computer 410 on which DPA client 138 is loaded and executing. DPA client 138 may further include a workflow module 420 and a viewer module 422.

Workflow module 420 preferably is configured to employ certain aspects of previously known pathology information systems, using virtual representations. Workflow module 420 provides a the mechanism for managing the pathologists' workflow when processing cases, organizing cases, grouping cases, creating folders for sharing cases with others, and the like. In particular, workflow module 420 manages and processes information from a set of workflow menus 424. More details of the function of workflow module 420 are described in the context of workflow menus 424, examples of which are described with reference to FIGS. 5 through 12.

Viewer module 422 is arranged for data presentation that visually resembles aspects of items and equipment that were previously employed by pathologists when using physical slides and microscopes, and/or is configured to operate functionally in a way that emulates the pathologists' operation of slide navigation tools and case package management practices that were employed with physical slides and microscopes. For this purpose, viewer module 422 manages and processes information from a set of viewer menus 426. More details of the function of viewer module 422 are described in the context of viewer menus 426, examples of which are described with reference to FIGS. 13 through 23B.

The user interface to pathology workstation 118 may include a first display 428 and a second display 430. For example, first display 428 may be a first computer monitor that is dedicated to the display of workflow menus 424 of workflow module 420 to a user 160, wherein workflow menus 424 are used for case management. Additionally, second display 430 may be a second computer monitor that is dedicated to the display of viewer menus 426 of viewer module 422 to the user 160, wherein viewer menus 426 are used for viewing and manipulating slide images. The combination of first display 428 and second display 430 may be considered to define a user cockpit 432 of pathology workstation 118.

The presence of two displays in user cockpit 432 of pathology workstation 118 is exemplary only and not meant to be limiting. For example, pathology workstation 118 may include a configuration of one display, two displays, three displays, and so on. The specific displays can be used with full screens devoted to different functions or split screen areas divided by function. The system can be arranged to shift automatically from displaying one function or another, or from one allocation of screens or screen areas to another allocation, when encountering particular control input signals or data values. Advantageously, at least the display or display screen area used for slide image viewing, has a pixel size and color resolution that is apt for diagnostic use.

Pathology workstation 118 may include additional user interface devices 434. For example, user interface devices 434 may include, but is not limited to, a standard computer keyboard (not shown), a standard computer mouse 436, and a slide-navigation device 438. Slide-navigation device 438 may be, for example, a commercially available or custom navigation device. For example, slide-navigation device 438 may be a mouse-like device that additionally includes a trackball and/or joystick mechanism.

The combination of mouse 436 and slide-navigation device 438 provide a dual input device configuration. For example, slide-navigation device 438 may be dedicated to performing "microscope tasks," such as image navigation, magnification, and focus. Slide-navigation device 438 is essentially the slide-navigation controller. By contrast, the separate mouse 436 may be used to perform standard point and click or scroll functions to handle computer user interface tasks while operating user cockpit 432. By having dual input devices, pathologists have input devices that are optimized for each type of task.

Client computer 410 may also include a processing unit 440; a quantity of local memory 442 for storing, for example, an image cache 444, which is a local image cache of macro-slide images 124 and/or micro-slide images 126 of the current session. Processing unit 440 and memory 442 may be used for managing the overall operations of client computer 410.

Processing unit 440 may comprise a standard controller or microprocessor device that is capable of executing program instructions loaded from disk or from the network into program memory, such as instructions from DPA client 138. Memory 442 may comprise any of the available data storage mechanisms capable of storing digital information that is processed locally or provided by data communications with client computer 410. For example, an image cache 444 may be provided in memory 442 or in a separate display driver memory. Image cache 444 may be employed as the local cache of macro-slide images 124, micro-slide images 126, and/or portions thereof that are being viewed and/or processed during the current session.

Referring to FIG. 4, workflow module 420 and viewer module 422 of DPA client 138 are the software modules that are in communication with DPA services 112 of workflow server 110. That is, workflow module 420 and viewer module 422 of DPA client 138 are sending requests to and processing information that is returned from DPA services 112 of workflow server 110. For example, when pathology workstation 118 requests an image (a macro-slide image 124 and/or micro-slide image 126), workflow server 110 processes the request to determine which diagnostic archive server 116 has stored or has access to the image and returns the path or similar addressing information to the requesting pathology workstation 118. The pathology workstation 118 then communicates with streaming services 134 of the source diagnostic archive server 116 and the requested macro-slide image 124 and/or micro-slide image 126 is streamed to the requesting pathology workstation 118. In this context, "streaming" may comprise packetized streaming as understood in connection with TCP/IP streaming protocols, or simply the sequential transmission of image data in compressed or uncompressed form, in serial or parallel data formats or in a hybrid of two or more of these forms or formats.

Figure 5:
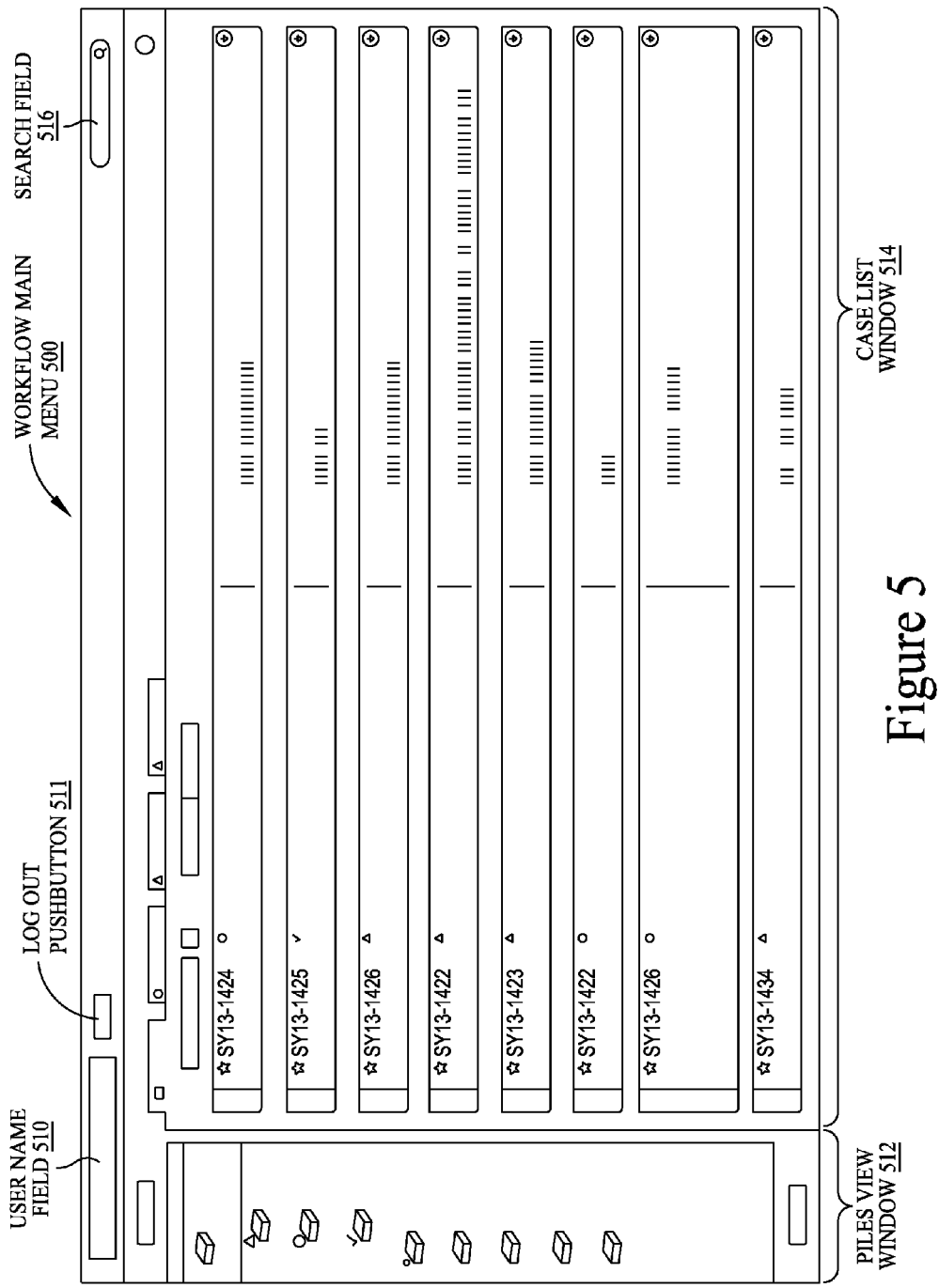
FIG. 5 shows an example of a workflow main menu of the digital pathology system.

FIG. 5 shows a workflow main menu 500, which is an example of a workflow menu 424 of workflow module 420 of DPA client 138. Workflow main menu 500 is an example of a menu by which users are able to see an overview of their work and may manage their caseload. For example, workflow main menu 500 displays the pathologist's case list, i.e. all of the cases that have been accessioned to the pathologist who is logged on to the system.

Workflow main menu 500 may include a user name field 510. Once a standard login process has been completed, the name and affiliation of a certain user 160 (e.g., a certain pathologist) may be displayed in user name field 510. In the depicted example, a hypothetical "Dr. David Parks, UPMC" is displayed in user name field 510, indicating that Dr. David Parks of the University of Pittsburgh Medical Center is the pathologist who is logged into digital pathology system 100, and can be one of a number of pathologists and organizations that are served, concurrently or sequentially. User authentication processes are presumed to have allowed Dr. Parks to log on, and a log out pushbutton 511 or other logoff process or signally technique is provided by which the user 160 may log out and end the session.

Workflow main menu 500 may also include a piles-view window 512 and a case-list window 514. The piles view window 512 can display a list of all cases that are currently in accession to the pathologist who is logged onto the system. Case list window 514 shows a summary view of each case. More details of piles view window 512 and case list window 514 of workflow main menu 500 are described with reference to FIGS. 6 and 7, respectively.

Workflow main menu 500 provides a search field 516, by which user 160 may enter any search term of interest, such as a patient name, doctor name, case number, and the like. Search field 516 may be used to perform a free-text search of cases. The search function may access any cases from any pile in piles view window 512. The search function may also include the capability to search text from case details. In one example, the search function, using search field 516, may be used to search for a patient by medical record number (MRN). When a search is performed the results may appear in a new tab. The search results may be presented as a list of cases and may look similar to cases in case list window 514. The search capability can provide one means by which cases are placed in accession to the user, e.g., the user searches for cases indicating that he/she is assigned to provide a diagnosis. This aspect is comparable to the traditional pathologist being handed a number of case packages.

Figure 6:
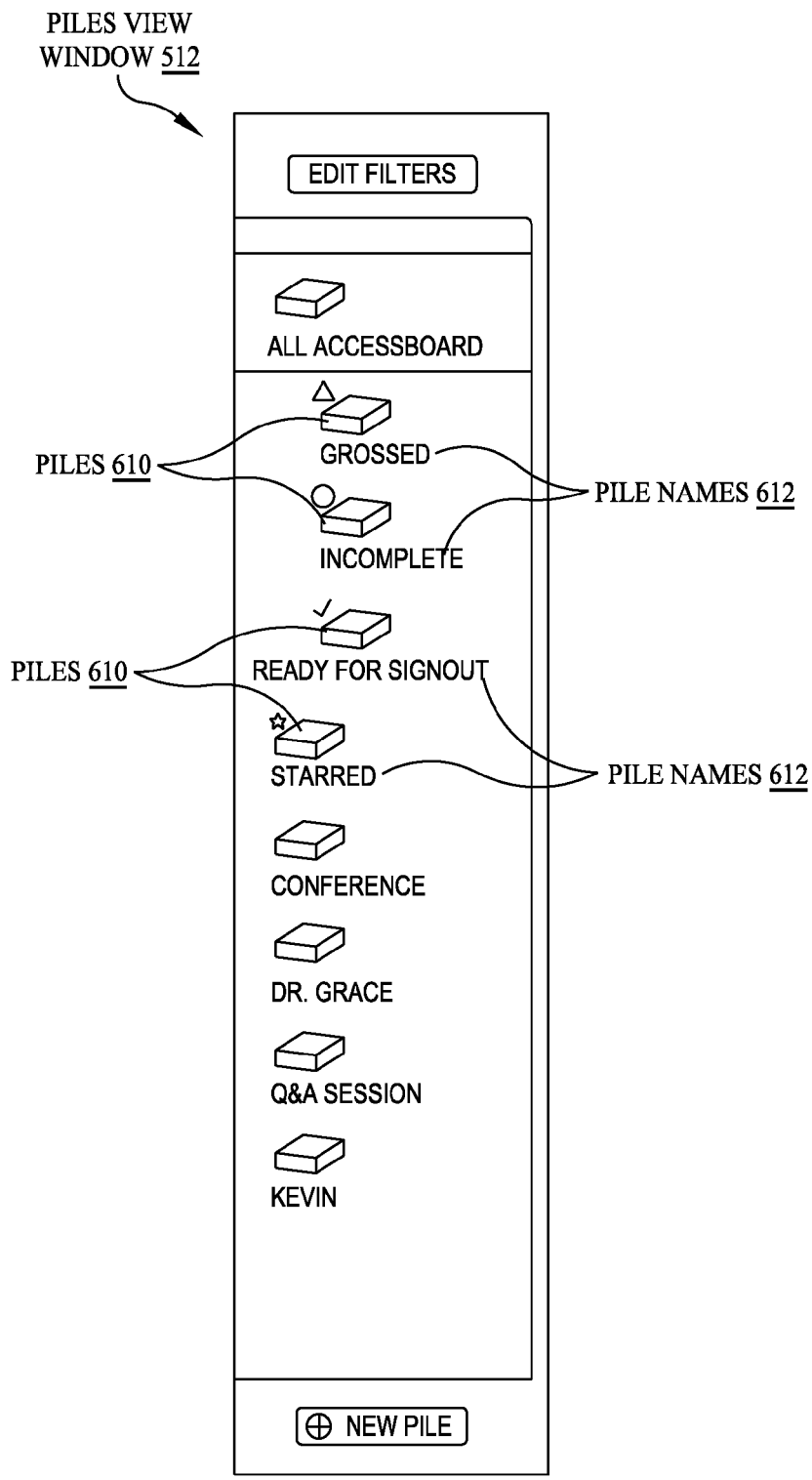
FIG. 6 shows an example a piles view window of the workflow main menu of the digital pathology system.

FIG. 6 shows an example of more details of piles view window 512 of workflow main menu 500. Piles view window 512 may include icons that depict one or more piles 610 having respective pile names 612. Piles 610 allow pathologists to categorize and organize their work. Piles 610 emulate the traditional behavior of pathologists who often organize case packages by categories, into physical piles. Piles 610 according to the invention actually represent a number of computer data files and associated information distributed through the computer system. The icons that depict piles 610 provide a familiar visualization to the user that resembles and/or substantially mimics physical case packages that are organized in physical piles, preferably as to how the icons appear and how they are moved about, albeit that piles 610 allow the user to access case information in electronic form rather than in physical form. Each pile 610 represents a collection of one or more cases, distinguishable by its pile name 612, representing a category description or an arbitrary name. Under the control of administrator component 212 of DPA services 112 of workflow server 110, as part of the pathology workflow, an administrator (not shown) assigns cases to each user 160. Therefore, when a certain user 160 logs into digital pathology system 100, the cases to which he/she as been assigned may automatically flow into piles 610 of piles view window 512 to be accessed by the user 160.

Digital pathology system 100 may provide certain default piles 610, such as certain default piles 610 having pile names 612 of "Grossed," meaning cases that are ready for diagnosis; "Incomplete," meaning cases that are assigned but for some reason are not ready for diagnosis; and "Ready for Signout," meaning cases that have been reviewed and are awaiting a final signature. Additionally, users 160 may create special or custom piles, similar to the way a computer user may create file folders. For example, a special pile 610 that has a pile name 612 of "Starred," meaning cases that have been distinguished by the pathologist as important for some reason; a special pile 610 that has a pile name 612 of "Second Opinion," meaning cases that have been sent to the pathologist by another pathologist; and so on. Certain piles may be defined by digital pathology system 100 that are not related to case status. For example, a pile 610 that has a pile name 612 of "All Accessioned," meaning all cases that have been assigned to the pathologist. When a certain pile 610 is selected, the cases that are contained in the selected pile 610 are displayed in case list window 514. It is an aspect of the digital presentation of the piles and cases that the piles may be categorized to permit the same case to be a member of more than one pile, which departs from strict resemblance to the piling of physical files but this versatility has benefits.

Further, a feature of piles view window 512 may be that a count of the number of cases contained in a certain pile 610 may be indicated alongside its associated pile name 612. By way of example, FIG. 6 shows a certain pile 610 that has a pile name 612 of "Grossed (25)," meaning twenty five cases are in this pile; another pile 610 that has a pile name 612 of "Incomplete (5)," meaning five cases are in this pile; another pile 610 that has a pile name 612 of "Ready for Signout (20)," meaning twenty cases are in this pile; and so on. In deference to the physical world, it would also be possible to cause the piles with more cases to appear higher or otherwise larger than the piles with fewer cases.

In one embodiment, the piles 610 are the same in size but include other color-coded iconography that helps pathologists quickly to associate piles and cases. For example, the "Grossed" pile 610 as shown also includes a colored arrow symbol (e.g., pink), the "Incomplete" pile 610 also includes a distinctly-colored clock symbol (e.g., blue), the "Ready for Signout" pile 610 also includes another colored checkmark symbol (green for go), the "Starred" pile 610 also includes star symbol (yellow for caution), and so on.

Figure 7:
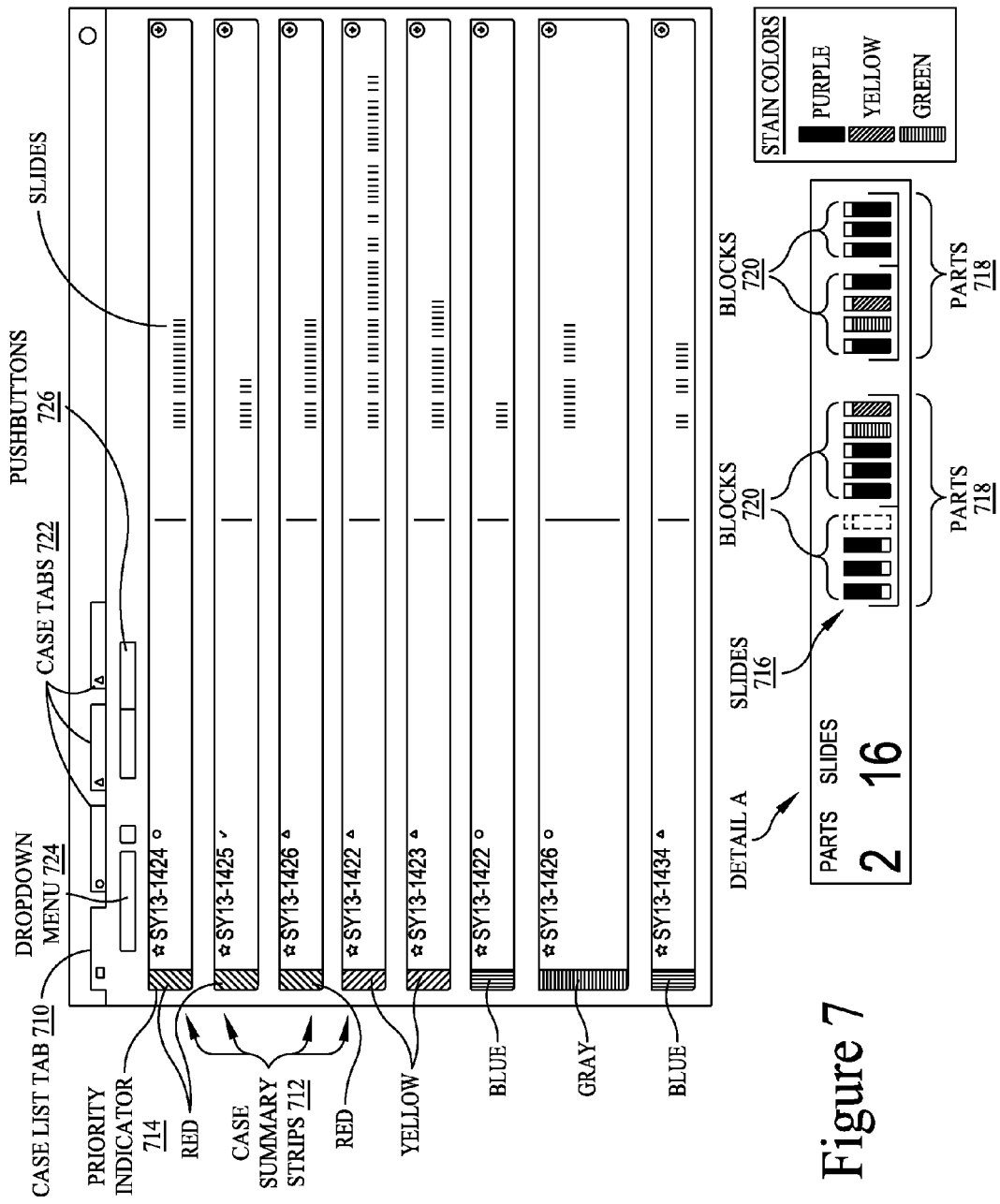
FIG. 7 shows an example of a case list window of the workflow main menu of the digital pathology system.
Figures 8A, 8B:
FIGS. 8A, 8B, 8C, and 8D show examples of case summary strips of the workflow main menu in the expanded state.
Figures 8C, 8D:

FIG. 7 shows an example of more details of case list window 514 of workflow main menu 500. Where piles view window 512 of workflow main menu 500 displays a pile-level view to the user 160, case list window 514 of workflow main menu 500 displays a case summary-level view of each case to the user 160. When a certain pile 610 in piles view window 512 is selected, the cases that are contained in the selected pile 610 are displayed in case list window 514. Each case in case list window 514 is represented by a case summary strip 712 that contains information about the case.

For example, case list window 514 includes a case list tab 710 that when selected displays a set of case summary strips 712 in a viewing window that correspond to the selected pile 610. A portion (e.g., a priority indicator 714) of each case summary strip 712 may be color coded in a manner that allows the pathologist to quickly determine at a glance the priority of each case. For example, the priority indicator 714 of certain case summary strips 712 may be color coded to indicate a priority of STAT (e.g., red), which in medical terms implies urgency. The priority indicator 714 of certain case summary strips 712 may be color coded to indicate a priority of RUSH (orange or yellow). The priority indicator 714 of certain case summary strips 712 may be color coded to indicate a priority of ROUTINE (light blue). Of these examples, STAT may be the highest priority, RUSH may be the midlevel priority, and ROUTINE may be the lowest priority.

A portion of each case summary strip 712 may include case-specific textual information, a non-limiting example being as follows:

an accession number (e.g., SY13-1424), which is the pathology case number. This is the primary means of identifying a case and is, thus, given prominence in position and text size;

the pile name 612 of the pile 610 in which the case is organized (e.g., Incomplete);

the patient's name;

the clinician's name, which is the doctor or surgeon who ordered the case;

a medical record number (MRN), which is a unique medical ID number for the patient; and case type information (e.g., biopsy, non-biopsy, or consult).

The source of this information is workflow database 136 of workflow server 110. In particular, DPA services 112 of workflow server 110 processes the request for case information when workflow main menu 500 is accessed via DPA client 138 of a certain pathology workstation 118.

Each case summary strip 712 may also include graphical information, such as, but not limited to, the same color-coded iconography that is shown in piles view window 512 of workflow main menu 500 that allows pathologists to quickly associate piles and cases. For example, certain case summary strips 712 may include the pink arrow symbol of the "Grossed" pile 610, the blue clock symbol of the "Incomplete" pile 610, the green checkmark symbol of the "Ready for Signout" pile 610, the yellow star symbol of the "Starred" pile 610, and so on. This graphical information correlates to the pile name 612 information in each case summary strip 712. Based on user input, the icons are selected and alteration of the icons may occur due to user input and/or by operation of the digital processor, so as to reflect the ongoing work and progress of review of images and case packages by the user.

Another portion of each case summary strip 712 may include icons that depict one or more slides 716 that are associated with the case. Slides 716 may be graphically arranged to provide familiar visualization to the user that resembles and/or substantially mimics glass slides arranged in slide trays that are used in physical microscope systems.

In physical pathology systems, glass slides are used to hold stained tissue or fluid smears. As suggested by shading in Detail A of FIG. 7, the graphical representation of slides 716 may be visually coded to indicate certain types of stains, preferably using colors that are suggestive of the type of stain. For example, a purple slide 716 may be used to indicate a hematoxylin and eosin (H&E) stain. An aqua slide 716 may be used to indicate an immunohistochemical stain. An orange slide 716 may be used to indicate any other special stain. In the graphical representation, some slide positions are shown as phantoms with an outline only. These are slides that are absent but are of significance in the case packages, such as slides that have been ordered but are not yet available in the system (i.e., slides that have not yet been scanned).

In physical pathology systems, samples are sometimes identified using terminology that distinguishes parts and blocks, as well as slides. The real world equivalents of parts may be body parts. Sets of associated samples from a body part such as a block of samples that are nearby or adjacent or of a given anatomical type are blocks. The slides are the single viewable samples mounted on a glass slide under a cover slip. Referring again to Detail A, digital pathology system 100 provides a hierarchy of visual elements that resemble the hierarchy of elements in physical pathology systems. By way of example, the set of 16 slides 716 that is shown in Detail A includes, for example, two parts 718. Further, each of the two parts 718 includes two blocks 720. The blocks can include multiple slides.

In physical pathology systems, slides are labeled near one end. Pathologists may turn a slide upside down after viewing the slide as a means physically to represent that the slide has been examined. Referring again to Detail A, digital pathology system 100 mimics this practice by indicating the "viewed" or "not viewed" state of each slide 716 via the orientation of the icon that is representing each slide 716. For example, when the slide "label" or distinctly marked end of the icon that is representing a certain slide 716 is oriented downward, this may indicate that the slide 716 is in a "viewed" state, meaning that user 160 already has examined that slide 716. By contrast, when the "slide label" of the icon that is representing a certain slide 716 is oriented upward, this may indicate that the slide 716 is in a "not viewed" state, meaning that user 160 has not yet examined the slide 716.

All the aforementioned visual features of slides 716 are examples of specific visual presentations and icon orientations that are varied in association with the pathologists' review of cases, allowing the pathologists to determine at a glance certain information about cases and/or about the slides in a case. These specific visual features are exemplary and are not intended as an exhaustive or limiting list of techniques by which visual aspects such as shape, size, orientation, color saturation or hue, display duty cycle blinking, animation, position, movement or any other possible visual features may be used according to this disclosure, for graphically indicating that particular slides or other aspects of a case are to be associated with a corresponding attribute or datum of information.

Certain case list controls are provided in case list window 514. For example, a "Sort by" dropdown menu 724 is provided that allows the case list to be sorted, for example by: Priority, Status, Case Type, Number of Slides, Accession Number, Accession Date, Patient Name, Clinician Name, Resident Name, and so on. Additionally, because some users 160 may prefer all of their cases to be either collapsed or expanded, "Expand All" and "Collapse All" pushbuttons 726 are provided that allow users to quickly set all cases to their preferred display status size. For example, the information that is shown in case summary strips 712 of case list window 514 of FIG. 7 corresponds to collapsed state. FIGS. 8A, 8B, 8C, and 8D show examples of case summary strips 712 in the expanded state. Additional information that is shown when case summary strips 712 are in the expanded state may include, for example, the accessioned date, the patient's gender and age, the resident or fellow assigned to the case, the number of previous pathology cases that the patient has had, a list of the names of the parts, and so on.

Figure 9:
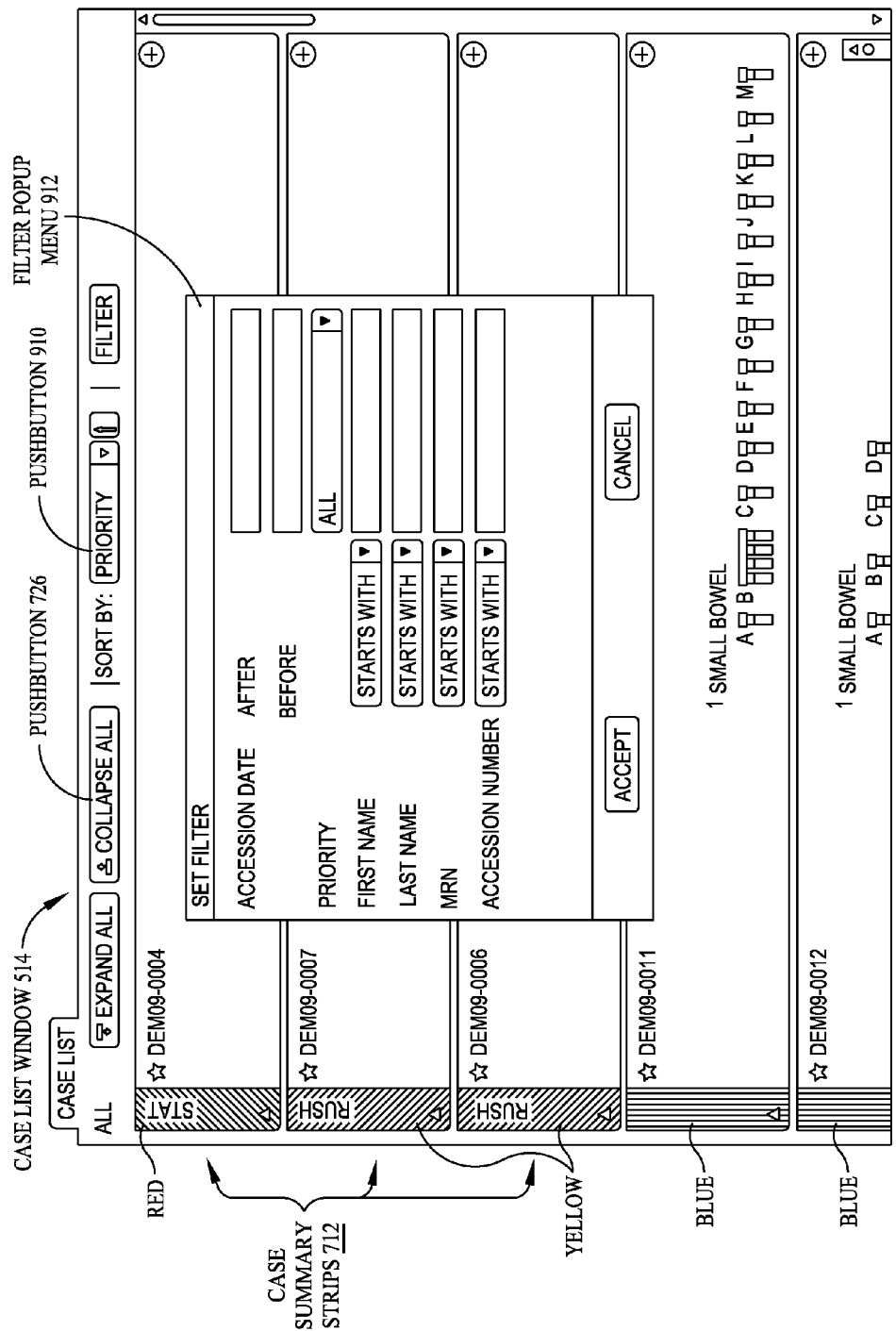
FIG. 9 shows a filter feature of the workflow main menu of the digital pathology system.

FIG. 9 shows a filter feature, which is another case list control. For example, FIG. 9 shows a filter pushbutton 910 that when pressed causes a filter popup menu 912 to be displayed to user 160. Filter popup menu 912 allows the user to filter cases by, for example, accession date, priority, full or partial first name, full or partial last name, full or partial MRN, full or partial accession number, and any combinations thereof. The filter settings for a certain user 160, is an example of information that may be stored in user data 242 of workflow database 136 of workflow server 110 and accessed during sessions by user preferences component 222 of DPA services 112.

With respect to other case list controls, although mouse 436 of pathology workstation 118 is intended as the primary input device, digital pathology system 100 provides mechanisms that allow users 160 to interact with the system using their preferred means of input, including the keyboard. Once case list window 514 is open, users 160 may use the up and down arrow keys of the keyboard to move through the cases. Pressing the space bar will toggle the case between expanded and collapsed mode. Pressing the enter key will open the details of the case, and so on.

When using case list window 514 of workflow main menu 500, case list tab 710 displays the case summary strips 712 of all cases of a selected pile 610 and allows user 160 to select one or more cases for review. The action of selecting a certain case summary strip 712 essentially opens the case for review and diagnosis by the pathologist. For each case that is opened, a case tab 722 is presented alongside the case list tab 710 within case list window 514. Each tab may labeled by accession number. Multiple cases can be open simultaneously. Therefore, multiple case tabs 722 may be presented within case list window 514. By way of example, FIG. 7 shows three case tabs 722, which indicates that user 160 has three cases open concurrently (e.g., SY13-1424, SY13-1431, and SY15-1431). When selected, each case tab 722 presents a view of detailed case information of the selected case. More details of the information presented in a case tab 722 are described with reference to FIGS. 10A and 10B.

In connection with cases that may be found in more than one pile 610, such as when piles can be defined as arbitrary subsets of the workload, a user can be provided with capabilities using mouse 436, for example, to drag and drop, copy and paste, insert and delete, etc., to associate remove or change the associations of a selected case summary strip 712 in case list window 514 with one or another of the piles 610 in piles view window 512.

Figure 10A:
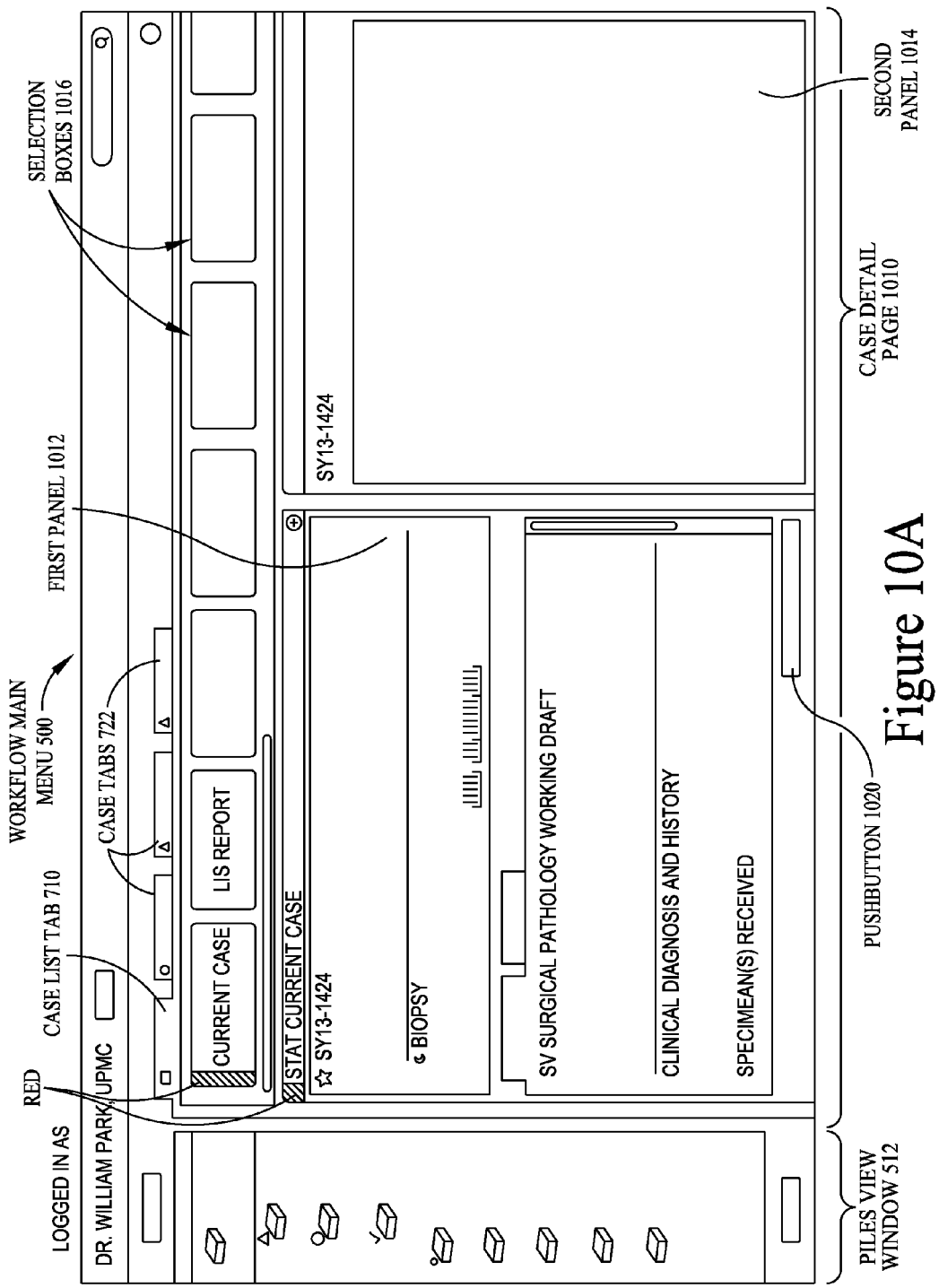
FIGS. 10A and 10B show an example of an expanded view of the case information of the workflow main menu of the digital pathology system.
Figure 10B:
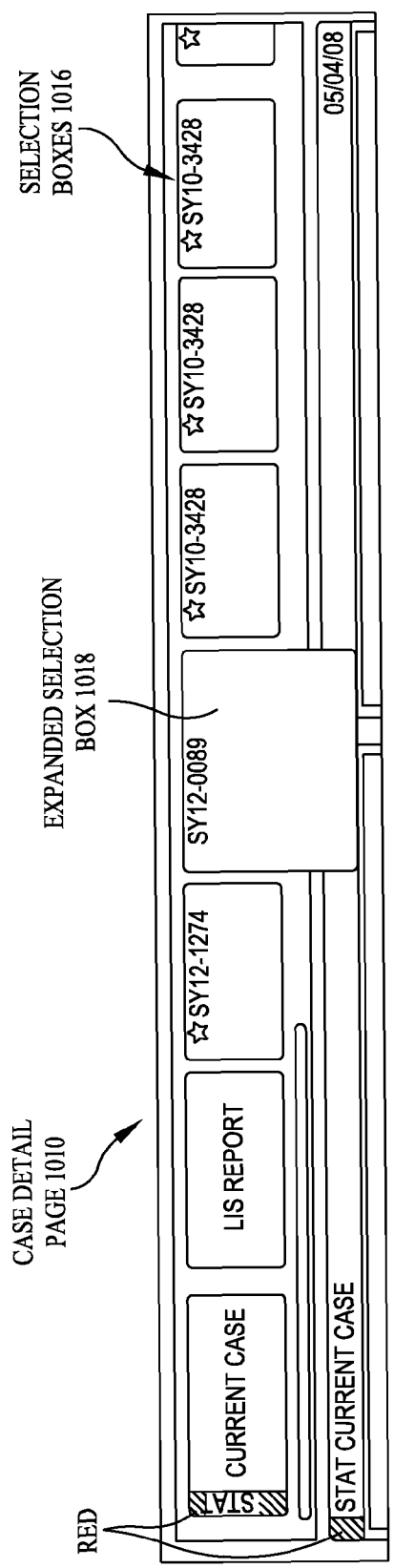

FIGS. 10A and 10B show an example of more details of an expanded view of the case information that may be presented to the user by selecting a certain case tab 722 of case list window 514 of workflow main menu 500. For example, FIG. 10A shows that the case tab 722 for case SY13-1424 is selected. An expanded view of the case information is presented in a case detail page 1010. Case detail page 1010 is organized, for example, into a first panel 1012 and a second panel 1014. Additionally, case detail page 1010 may include certain selection boxes 1016 by which the user may select the content to be presented in first panel 1012 and second panel 1014.

First panel 1012 and second panel 1014 allows user 160 to view various types of information in each panel as needed. For example, in one example there may be three basic types of information that can be displayed on each panel: Current Case, Report, and Past Cases. Therefore, above first panel 1012 and second panel 1014 is an arrangement of multiple selection boxes 1016. Selection boxes 1016 represent any possible items that can be displayed in first panel 1012 and second panel 1014. In one example, there may be a "Current Case" selection box 1016, a "Report" selection box 1016, and one or more "Past Case" selection boxes 1016. If there are more selection boxes 1016 than can be displayed at one time within the confines of case detail page 1010, a horizontal scrollbar appears below selection boxes 1016, which allows user 160 to navigate across all selection boxes 1016.

The contents of two selection boxes 1016 are always presented to user 160 because there are always two panels of information being displayed. In first panel 1012 and/or second panel 1014, if there is more content than can be displayed at one time within the confines of case detail page 1010, a vertical scrollbar appears beside first panel 1012 and/or second panel 1014, which allows user 160 to navigate through the content. Additionally, the positions of first panel 1012 and second panel 1014 may be rearranged on case detail page 1010 by dragging one panel over the other.

In one example, the information displayed in first panel 1012 may default to the contents of the "Current Case" selection box 1016. Further, the information displayed in second panel 1014 may default to the contents of the "Report" selection box 1016. However, pathologists may select any "Past Case" selection box 1016 to view information about past cases on either of the panels. Possible combinations of information that may be displayed in first panel 1012 and second panel 1014 at one time may include, but are not limited to, current case/report, current case/past case, past case/report, and past case/past case. The visualization of current cases vs. past cases may differ. For example, the color of the "Current Case" selection box 1016 may be blue, while the color of "Past Case" selection boxes 1016 may be gray. This is to help the pathologist to avoid confusing current case information with past case information.

FIG. 10A shows an exemplary default view of "Current Case" information in first panel 1012 and "Report" information in second panel 1014. With respect to "Report" information in second panel 1014, user 160 may enter any notes while performing the case review and potentially reaching a diagnosis. By use of reporting component 224 of DPA services 112 of workflow server 110, the information entered in second panel 1014 may be integrated into any reporting mechanism of digital pathology system 100. For example, reporting mechanisms may vary from one hospital to another. Therefore, reporting component 224 may be used to integrate "Report" information into any reporting mechanism by converting the content to any file format and/or data entry system.

Another feature of the case detail page 1010 in this embodiment, is the ability to hover over or "mouseover" an icon such as a past case icon, thereby causing the system to display a defined information set, such as a summary of the final diagnosis of the past case, without placing the full details in first panel 1012 or second panel 1014. An example of this is shown with reference to FIG. 10B. For example, FIG. 10B shows a portion of case detail page 1010 with a computer cursor, which is controlled by mouse 436 of pathology workstation 118, positioned by the user atop a certain "Past Case" selection box 1016. As a result, the size of the selection box 1016 is expanded (e.g., expanded selection box 1018) to show summary text of the final diagnosis of the past case.

In one example, there are two ways to select information to appear in first panel 1012 and second panel 1014—(1) by clicking on a selection box 1016 that is not currently selected may change first panel 1012 to contain the information associated with that selection box 1016. For example, clicking on a "Past Case" selection box 1016 may change first panel 1012 to display the information for that past case. Clicking a selection box 1016 always changes first panel 1012 because it is assumed that pathologists want to see current case information in first panel 1012 most of the time; and (2) by dragging a selection box 1016 to a specific panel will display the information associated with that selection box 1016 in that panel. This allows users to put specific information in the desired panel.

Figure 11:
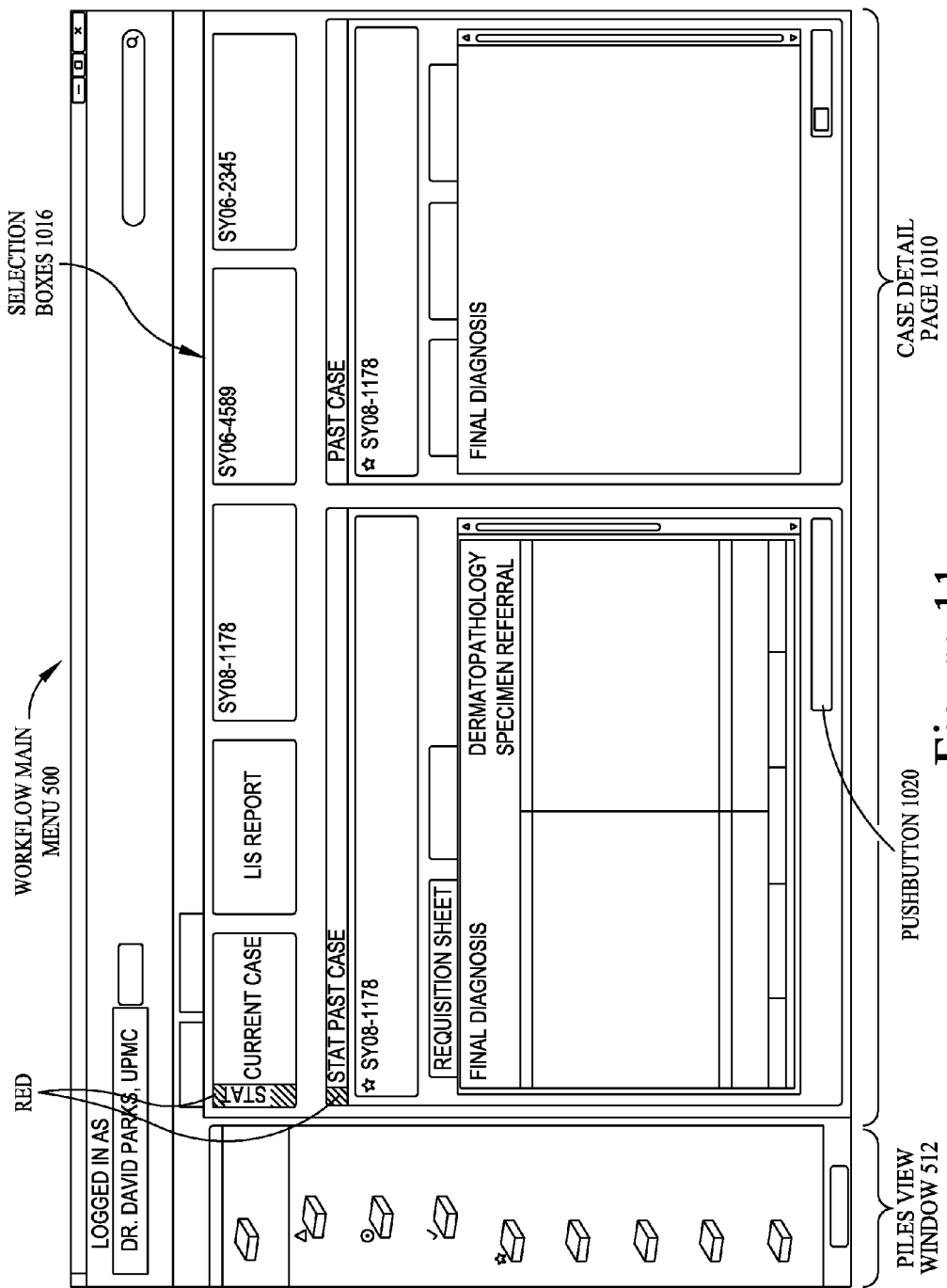
FIG. 11 shows a view of a case detail page of the workflow main menu of the digital pathology system.

FIG. 11 shows another view of case detail page 1010, wherein "Current Case" information is shown in first panel 1012 and "Past Case" information is shown in second panel 1014. Further to the example of "Current Case" information, first panel 1012 displays the case requisition sheet of the current case. This is an example of the ability to display any information about a case as long as it is provided in electronic form, such as a scan of the paper requisition sheet. Referring to FIGS. 10 and 11, along with the current case information, first panel 1012 also includes a "Mark as Ready for Signout" pushbutton 1020. Clicking on pushbutton 1020 marks the case as ready for signout and places it into the "Ready for Signout" pile 610 of piles view window 512. Clicking on pushbutton 1020 also closes the case detail.

Additionally, in this example, full details of the final report of the past case are displayed in second panel 1014. FIG. 12 shows a past case final report 1200, which is an example of an expanded view of a final report of the past case. A "Final Report" tab of case final report 1200 may show, for example, details of the case diagnosis as well as the date that the case was signed out. Case final report 1200 may also include a "Case information" tab for viewing the full case information and a "Requisition Sheet" tab for viewing the original requisition sheet.

Along with the textual information, past case final report 1200 in second panel 1014 also includes a "View Slides" pushbutton 1210. Clicking on pushbutton 1210 opens viewer menus 426 at second display 430 of user cockpit 432 of the pathology workstation 118, which allows user 160 to view the slides of the past case.

Referring again to FIGS. 5 through 12, the graphical menus shown therein are exemplary only of workflow menus 424 of workflow module 420 of DPA client 138 of each pathology workstation 118. The menus shown in FIGS. 5 through 12 are not meant to be limiting, any other menu designs that, preferably, attempt to resemble and/or mimic physical pathology systems and processes are possible.

Figure 13:
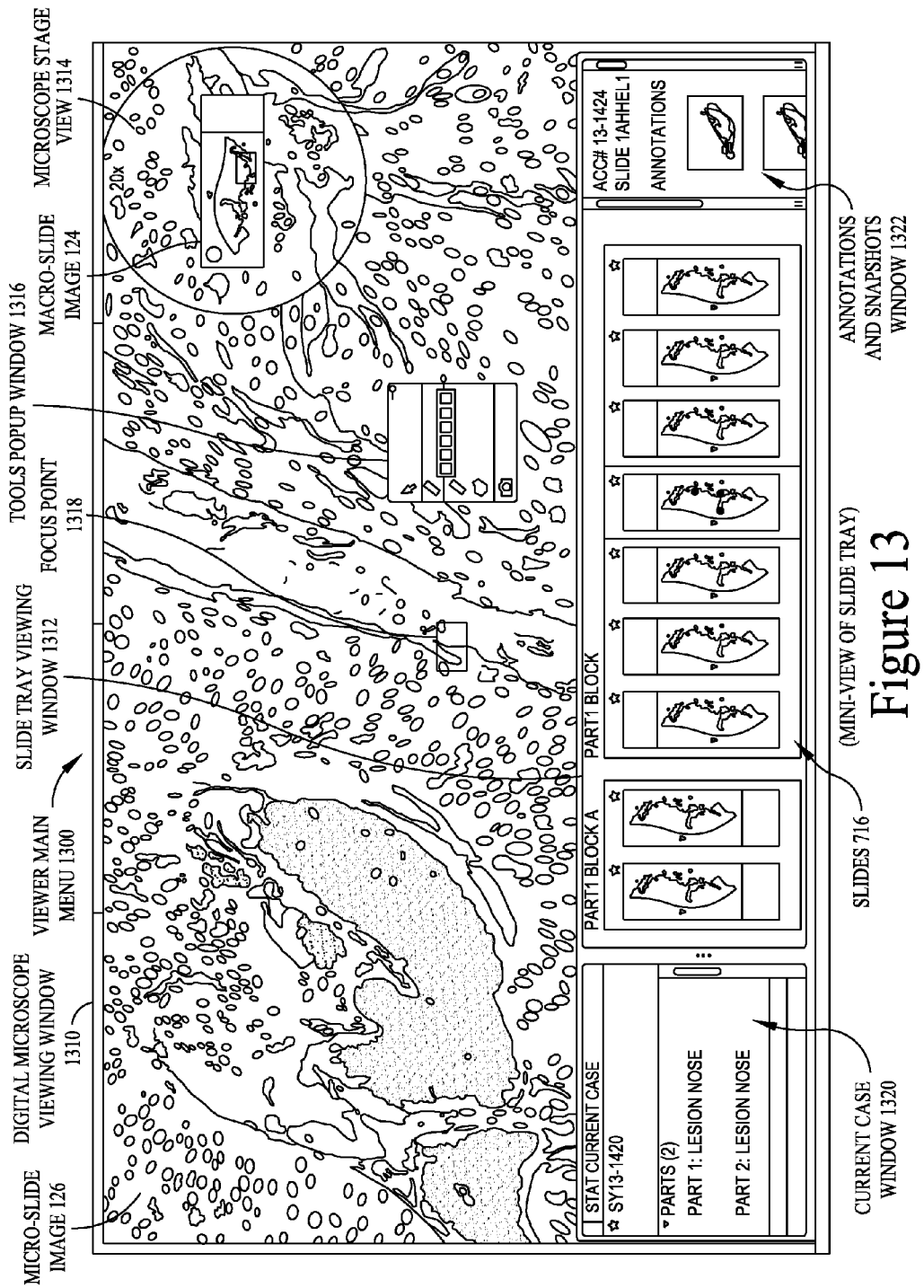
FIG. 13 shows an example of a viewer main menu of the digital pathology system.

FIG. 13 shows a viewer main menu 1300, which is an example of a viewer menu 426 of viewer module 422 of DPA client 138. Viewer main menu 1300 is an example of a menu by which users may view and manipulate slide images. For example, viewer main menu 1300 allows users 160, e.g., pathologists, to view slides 716 that are described with reference to FIGS. 5 through 12. Where workflow main menu 500 and other associated menus of FIGS. 5 through 12 display pile-level and case-level views to the user 160, viewer main menu 1300 and other associated menus display slide tray-level views of cases to the user 160. Again, the slide tray-level view is intended to provide a familiar visualization to the user that resembles and/or substantially mimics physical slide trays that are used in physical microscope systems.

The primary components of viewer main menu 1300 are, for example, a digital microscope viewing window 1310 and a slide tray viewing window 1312. Digital microscope viewing window 1310 is the viewing window for displaying micro-slide images 126 or portions thereof that correspond to a selected slide 716 of a selected case. In particular, digital microscope viewing window 1310 provides a familiar visualization to the user that resembles and/or substantially mimics the view of slides through a physical microscope. Similarly, slide tray viewing window 1312 provides a familiar visualization to the user that resembles and/or substantially mimics physical slide trays that are used in physical microscope systems.

A microscope stage view 1314 is overlaid atop a portion of digital microscope viewing window 1310. Microscope stage view 1314 provides a graphical representation of a physical microscope stage that has a slide resting thereon. For example, microscope stage view 1314 is shown with a graphical representation of a certain macro-slide image 124 resting thereon. The macro-slide image 124 corresponds to the selected slide 716. Microscope stage view 1314 may be used for slide navigation, which is further described with reference to FIGS. 16A and 16B.

Also shown overlaid atop a portion of digital microscope viewing window 1310 is a tools popup window 1316, which is further described with reference to FIGS. 17A, 17B, 18A, 18B, and 19. FIG. 13 shows a focus point 1318 that is held in a fixed position at a substantially central location within digital microscope viewing window 1310. Focus point 1318 provides a fixed reference point by which users 160 may orient themselves with respect to any view that is present in digital microscope viewing window 1310. In one example, focus point 1318 is a rectangular-shaped feature. With fast jerky slide movements and magnification jumps, it is easy to become disorientated or even nauseous. Focus point 1318 in the middle of digital microscope viewing window 1310 can provide a focus point for pathologists to help them cope with fast slide movements and prevents disorientation when zooming in. Additionally, pathologists are accustomed to focusing their eyes on the center of the view field when using a physical microscope.

Certain features of viewer main menu 1300, such as tools popup window 1316, may be toggled on and off by user 160. Additionally, the background of certain features of viewer main menu 1300, such as microscope stage view 1314, may be semi-transparent.

Slide tray viewing window 1312 is also shown overlaid atop a portion of digital microscope viewing window 1310. As a result, digital microscope viewing window 1310 is always the background of any other visualization provided within viewer main menu 1300. For the selected case, the icons of slides 716 that are described with reference to FIGS. 5 through 12 are displayed in slide tray viewing window 1312. Also displayed in slide tray viewing window 1312 is current case window 1320 and an annotations and snapshots window 1322.

Displayed in current case window 1320 is case summary information that mirrors the case information shown in workflow main menu 500 and the associated menus of FIGS. 5 through 12. Displayed in annotations and snapshots window 1322 are annotations and snapshots of any portions of slides 716 that have been annotated or otherwise captured. All annotations and snapshots get added to the top of annotations and snapshots window 1322 as soon as they are created. When there are no annotations or no snapshots, a message appears in the respective area with instructions on how to make an annotation or take a snapshot. More details of the annotations and snapshots feature of digital pathology system 100 are described with reference to FIGS. 17A, 17B, 18A, 18B, and 19.

Slide tray viewing window 1312, which is shown atop a portion of digital microscope viewing window 1310, may be displayed to various degrees as selected by user 160. For example, there may be a fully expanded view, a mini-view, and a fully collapsed view of slide tray viewing window 1312.

FIG. 13 shows slide tray viewing window 1312 in the mini-view state, where, for example, a limited number of slides 716 are shown, a portion only of the information in current case window 1320 is shown, and a limited number of snapshots are shown in annotations and snapshots window 1322. In the mini-view of slide tray viewing window 1312, vertical scroll bars may be provided that allow user 160 to scroll through and view all information.

Figure 14A:
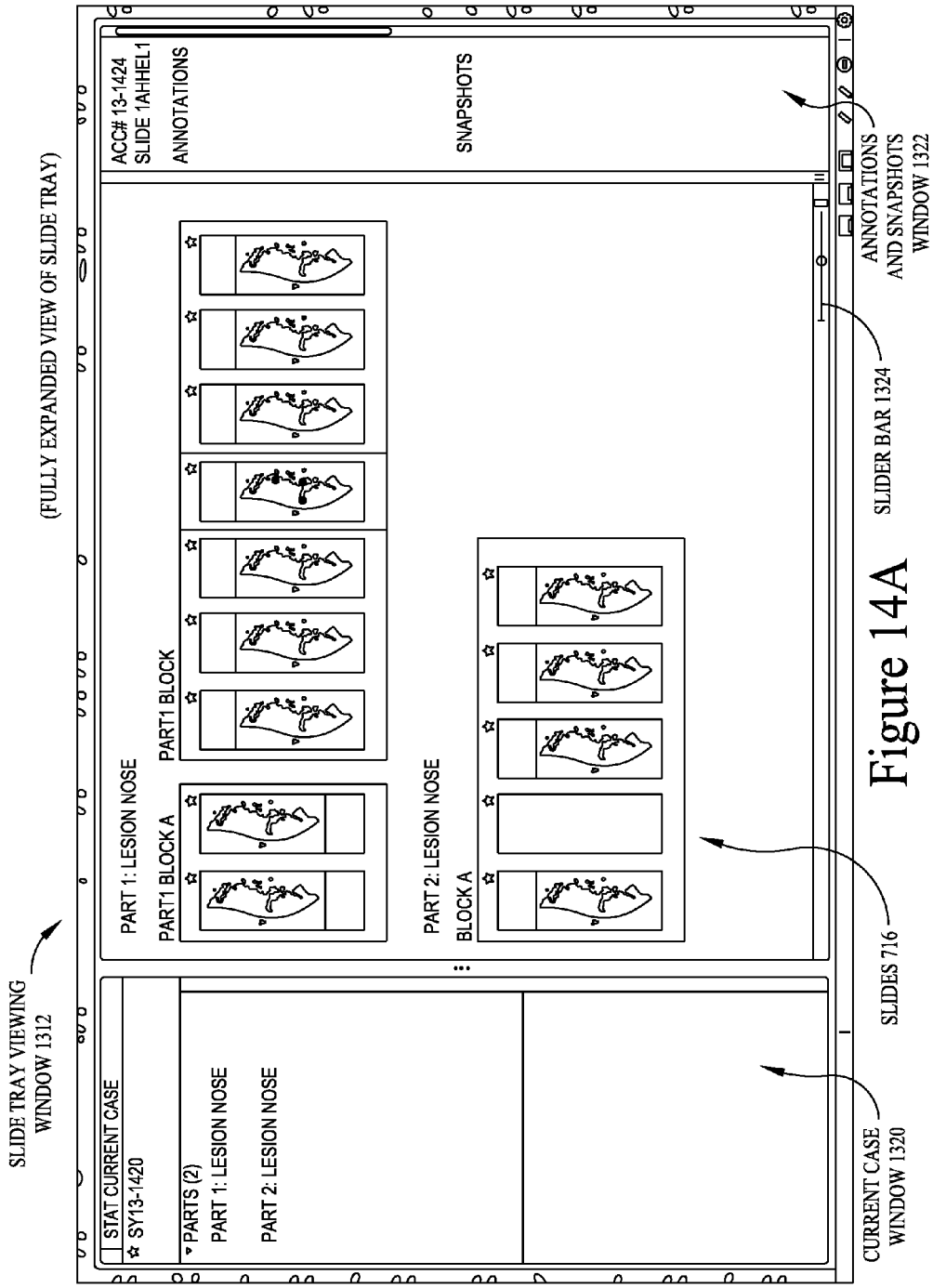
FIG. 14A shows a fully expanded view of a slide tray viewing window of the viewer main menu of the digital pathology system.

FIG. 14A shows slide tray viewing window 1312 in the fully expanded view state, where, for example, all slides 716 are shown, all information in current case window 1320 is shown, and all snapshots are shown in annotations and snapshots window 1322. In the fully expanded view state, FIG. 14A shows a slider bar 1324 that allows the user to control the size of slides 716 in slide tray viewing window 1312. Slider bar 1324 allows pathologists to adjust the size of slides 716 according to their own preference and physical setup. Again, this is a preference that may be saved in user data 242 of workflow database 136 of workflow server 110 and accessed during sessions by user preferences component 222 of DPA services 112.

Figure 14B:
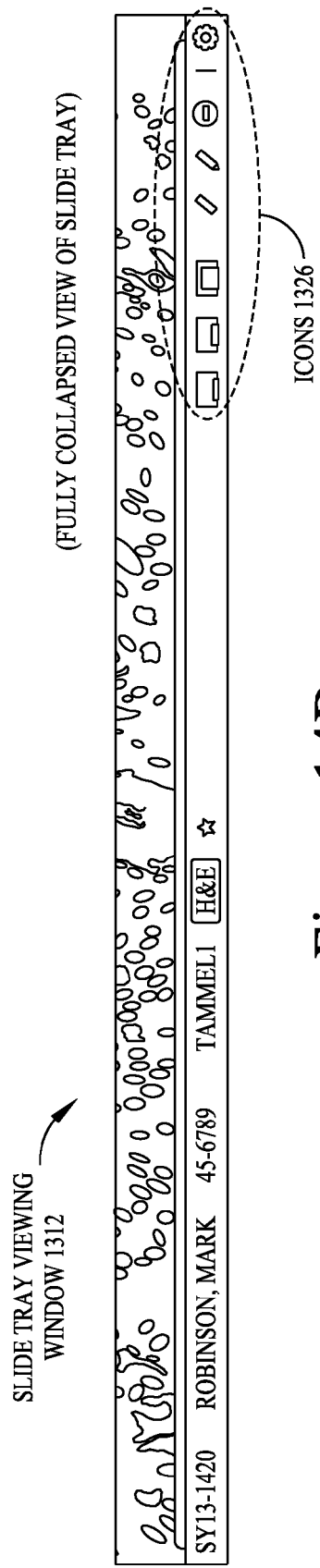
FIG. 14B shows a fully collapsed view of the slide tray viewing window of the viewer main menu of the digital pathology system.

FIG. 14B shows slide tray viewing window 1312 in the fully collapsed view state, where, for example, no slides 716 are shown, no information in current case window 1320 is shown, and no snapshots are shown in annotations and snapshots window 1322.

Because slide tray viewing window 1312 is overlaid atop a portion of digital microscope viewing window 1310, in the fully expanded view, the least amount of viewing area is made available in digital microscope viewing window 1310. The fully collapsed view results in a relatively larger viewing area in digital microscope viewing window 1310. The mini-view results in an intermediate allocation of space, i.e., the amount of viewing area in digital microscope viewing window 1310 is greater in mini-view mode than in the fully expanded view and less than in the fully collapsed view of slide tray viewing window 1312.

The display of slide tray viewing window 1312 may be toggled via a key command. When slide tray viewing window 1312 is either in the fully expanded view or mini-view state, the user operates a key such as an assigned keyboard function "F" key to toggle to the fully collapsed view. When slide tray viewing window 1312 is in the fully collapsed view, the view toggles to the mini-view state when the key command is used. Preferably, the key command is not involved in putting slide tray viewing window 1312 into the fully expanded view state. More details of the key commands for toggling the state of slide tray viewing window 1312 are explained with reference to the example keyboard shortcuts and FIG. 20.

Certain icons on the status bar of viewer main menu 1300 may indicate the current state of slide tray viewing window 1312 and allow the display of slide tray viewing window 1312 to be changed to any of its three states. For example, FIG. 14B shows an example of a set of icons 1326 for indicating and/or toggling the state of slide tray viewing window 1312.

Referring to FIGS. 13, 14A, and 14B, when a case is selected and opened at first display 428 using workflow main menu 500 and the associated menus of FIGS. 5 through 12, the associated case information and slides 716 are automatically read into digital microscope viewing window 1310 and slide tray viewing window 1312 of viewer main menu 1300 of second display 430. In this way, the necessary information and slides are automatically ready for the pathologist to review and process. In one example, when a case is opened, the default view of slide tray viewing window 1312 may be the fully expanded view and the first slide 716 in the case may be the default slide that is presented in digital microscope viewing window 1310. Further, the arrangement of the slides 716 by parts and blocks (see Detail A of FIG. 7) is maintained from workflow main menu 500 at first display 428 to viewer main menu 1300 at second display 430.

FIGS. 15A through 15E show examples of individual slides 716 in some different states. Each slide 716 includes the scanned image of the label of the original glass slide 132. The label is oriented upward so long as the slide 716 has yet to be viewed. An example of a slide 716 in the unviewed state is shown in FIG. 15A. The label is oriented downward after the slide 716 has been viewed. An example of a slide 716 in the viewed state is shown in FIG. 15B. In either case, the label is always oriented right side up so that it can be read by the pathologist.

Displayed above each slide 716 may be the slide number and, for example, the star icon, which indicates a slide that has been flagged with a star for some purpose such as particular importance. Displayed below each slide 716 may be certain icons indicating how many annotations and snapshots have been taken on that slide. These icons do not appear if there are no annotations and/or snapshots for the slide 716. When annotations are present on a certain slide 716, the annotations are visible as dots on the image of the slide 716. For example, FIG. 15B shows a slide 716 with one dot, which indicates one annotation.

FIG. 15C shows a slide 716 that is highlighted in blue, which indicates that the slide 716 is currently being viewed in digital microscope viewing window 1310 (i.e., a currently being viewed state). The current slide 716 that is being viewed is highlighted in blue and is slightly bigger than the other slides 716. When a case is first opened, the first slide 716 of the case is highlighted blue because it is the slide 716 that is currently being viewed. Double clicking on a certain slide 716 selects that slide to be presented as the currently viewed slide. A key command may also be used to select a currently viewed slide. More details of the key commands for changing the currently viewed slide 716 are shown with reference to the example keyboard shortcuts of FIG. 20.

FIG. 15D shows a slide 716 that is highlighted in gray to indicate a selected slide (i.e., the highlighting indicates the "selected" state). A certain slide 716 may be selected, but the selected slide need not also be the currently viewed slide. These states can be distinct. The selected slide 716 is highlighted in gray unless it is also being viewed in which case it remains highlighted in blue. If a certain slide 716 is selected, the snap shots and annotations for the selected slide 716 appear in annotations and snapshots window 1322 of slide tray viewing window 1312. Single clicking on a certain slide 716 selects it. However, when the slide 716 that is currently being viewed changes, the new slide being viewed automatically becomes the selected slide 716. If the user clicks on the background of the slide area of slide tray viewing window 1312, the selected slide becomes unselected and the annotations and snapshots of the entire case appear in annotations and snapshots window 1322.

A slide that is on order but has not yet been scanned and/or entered into the system image data storage can be assigned an identity in the database of stored slide information, but preferably appears in slide tray viewing window 1312 as a "ghost." An example of a slide 716 in the ghost slide state is shown in FIG. 15E. No image is yet available, but the ghost slide has various known attributes such as a part, block, description as to stain, etc., because these were ordered, an unviewed status, etc.

Referring to FIGS. 1 through 15E, digital pathology system 100 is optimized for a dual input device setup, such as for the use of mouse 436 and slide-navigation device 438. Slide-navigation device 438 is dedicated to "microscope" actions, such as image navigation, magnification, and focus. A separate device, such as mouse 436, is used to control the user interface.

With respect to image panning, the primary means of panning across an image is by manipulating slide-navigation device 438. Preferably, slide-navigation device 438 is always active and may pan the image regardless of what part of digital microscope viewing window 1310 has focus. Alternatively, the user 160 may pan across the image by clicking and dragging with mouse 436. This method is well understood by pathologists and common across digital pathology and other image viewing applications. It provides a useful backup method in circumstances in which slide-navigation device 438 is not available.

Figures 16A, 16B:
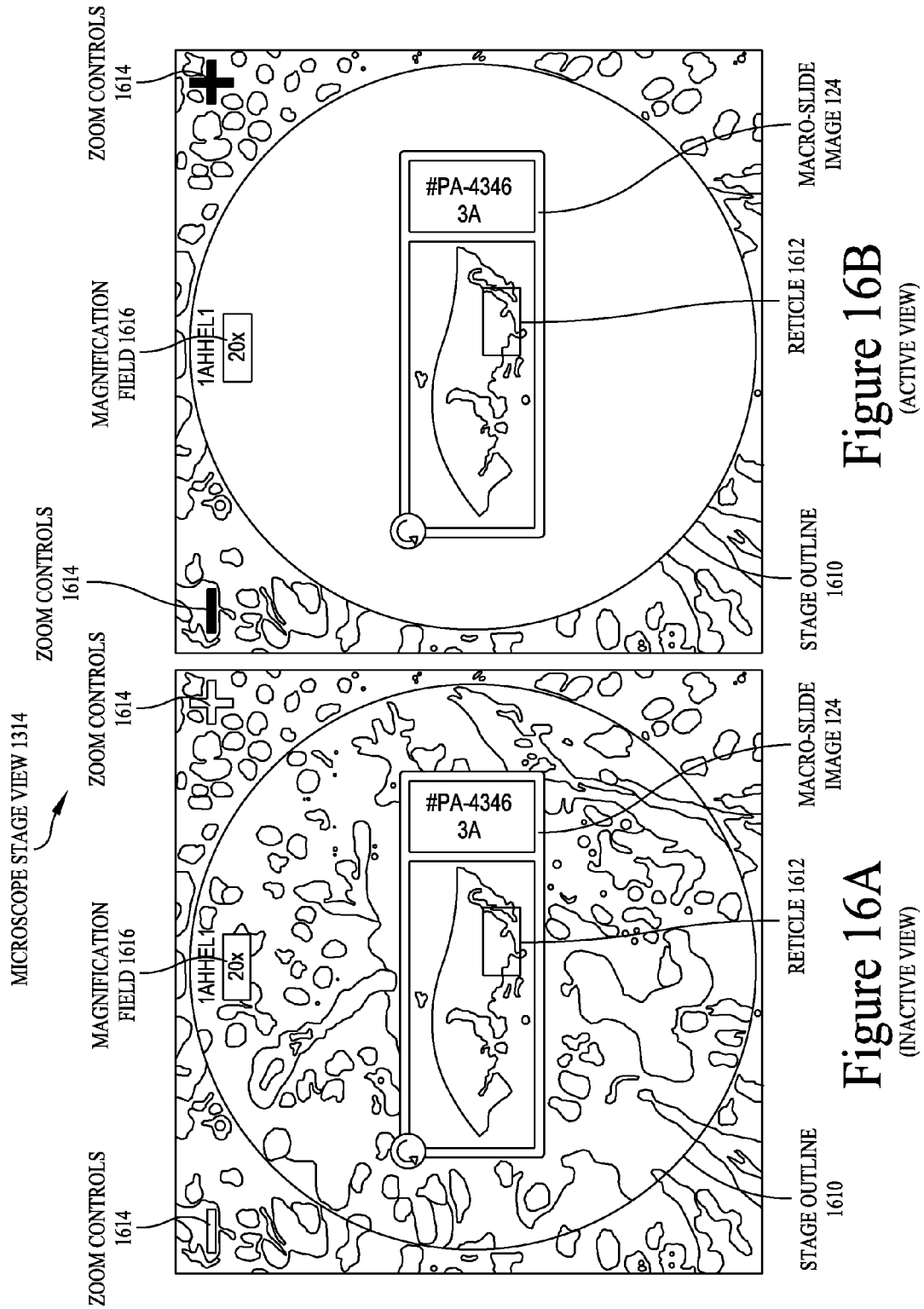
FIGS. 16A and 16B show details of a microscope stage view of the viewer main menu of the digital pathology system.

FIGS. 16A and 16B show more details of microscope stage view 1314 of viewer main menu 1300. In particular, FIG. 16A shows microscope stage view 1314 in an inactive state and FIG. 16B shows microscope stage view 1314 in an active state. The active state occurs via a "mouseover" or cursor hovering over microscope stage view 1314. That is when the computer cursor, which normally is controlled by mouse 436 of pathology workstation 118, is positioned atop microscope stage view 1314. Microscope stage view 1314 also has a third state, which is a collapsed state (not shown).

FIGS. 16A and 16B show that microscope stage view 1314 may include a stage outline 1610, which visually resembles the outline of a physical microscope stage and/or substantially mimics the functional operation of a stage to displace the point of view in an X-Y direction. Within the boundaries of stage outline 1610 is an icon of a certain macro-slide image 124. In the inactive state, the background within stage outline 1610 is translucent to allow the tissue beneath to show through. In the active state, the background within stage outline 1610 is darkened and becomes less translucent, although it still retains a small degree of transparency. Also, an icon (not shown) may appear over the slide image to indicate that user 160 may rotate the slide image.

Within the boundaries of the certain macro-slide image 124 is a reticle 1612. A reticle in general is a superimposed representation of a grid or shape in fine lines when useful to point out the scale or position of what is being shown. Reticle 1612 may have, for example, two states. In one state, reticle 1612 may be rectangular shaped. In another state, reticle 1612 may be cross shaped. In either case, reticle 1612 preferably remains oriented parallel to the edges of digital microscope viewing window 1310, even as the slide is rotated on microscope stage view 1314. By dragging reticle 1612 on macro-slide image 124, users can pan across the slide image. The panning action is reflected in digital microscope viewing window 1310. Users can also jump to a specific point on the slide image by clicking on the corresponding area of the tissue shown on microscope stage view 1314.

Magnification is central to pathologist's work and therefore a core part of digital pathology system 100. There may be, for example, at least three ways to change magnification when viewing a slide image. A first way to change magnification is by pointing and clicking selected control buttons on slide-navigation device 438 using the mouse or other pointer. This is a preferred means of changing magnification. Specific button layouts are dependent on the slide-navigation device 438 that is being used. In one example, one control button on the slide-navigation device 438 increases magnification and control button decreases magnification. Another way to change magnification can be by using zoom controls 1614 (e.g., "–" and "+" buttons) on microscope stage view 1314. A third way to change magnification can be by using key commands to change magnification. More details of the key commands for changing the magnification are shown with reference to the example keyboard shortcuts of FIG. 20.

Magnification features of microscope stage view 1314 can be arranged in discrete intervals, similar to a physical microscope. The provided magnification levels may be, for example, "fit", 1×, 2×, 4×, 10×, 20×, and 40×. A "Fit" selection selects that the image is to be displayed at a magnification of 1× or lower (e.g. 0.5×) as needed so that the entire image can fit on digital microscope viewing window 1310 at one time. Inasmuch as the specific magnification may be varied by image processing calculation techniques to any ratio, it is also possible to make the magnification continuously adjustable. In that event, the image that is presented can be processed by decimating and spatially compressing, or by interpolating and spatially expanding, a stored image data set that is at a higher or lower pixel spatial resolution.

Referring again to FIGS. 16A and 16B, the current magnification level may be displayed in a magnification field 1616 of microscope stage view 1314. The background color of magnification field 1616 when arranged to display in one of the incrementally stepped magnification levels, can be color coded by a border that corresponds to the colored rings on the objectives of a physical microscope. The color mapping is, for example, 2×=white, 4×=red, 10×=yellow, 20×=light green, and 40×=dark green. Because 1× objectives are less common and there is no objective for "fit", the color-coding can be omitted for these magnification levels.

Reticle 1612 indicates the area of the slide image that is currently visible in digital microscope viewing window 1310. Therefore, the size of reticle 1612 on the slide image is smaller as the user increases magnification, and vice versa. The size of reticle 1612 is also affected by the resolution of the viewer's window. At high magnification, a rectangular reticle 1612 becomes too small to be easily seen or manipulated. Therefore, at, for example, 10× or 20× magnification reticle 1612 can be changed from a rectangle to a cross shape.

Microscope stage view 1314 serves at least three purposes: (1) it provides a thumbnail view of the selected slide 716, as described above; (2) it provides a means to rotate the slide image; and (3) is provides information about the slide 716 that is being viewed.

With respect to rotating the slide image, clicking and dragging the edges of the slide image on microscope stage view 1314 rotates the slide as well as the entire image being displayed in digital microscope viewing window 1310. The actual target area for clicking mouse 436 in order to rotate the slide extends slightly beyond the edges of the slide itself to provide a larger target area for the user. However, clicking the actual scan of the slide itself does not rotate the image since clicking in this area moves reticle 1612. If the slide label is present, it can also be clicked to rotate the image.

Because rotation is typically something that is done when a pathologist first looks at a slide, it is advantageous for the digital pathology system 100 to store the orientation of the slide. In this way, when user 160 goes to another slide (or even another case) and then returns to this slide, digital pathology system 100 remembers the slide's orientation and resumes the orientation that was selected.

Several pieces of information about the currently viewed slide are displayed in microscope stage view 1314 including, for example, the slide number, the slide's orientation, and the level of magnification. In addition, a photo of the slide's label can be displayed on the slide, which may also contain the slide number depending on the institution. Users 160 may choose whether or not to display this slide label and this preference information may be saved in user data 242 of workflow database 136 of workflow server 110 and accessed during sessions by user preferences component 222 of DPA services 112.

Figure 17A:
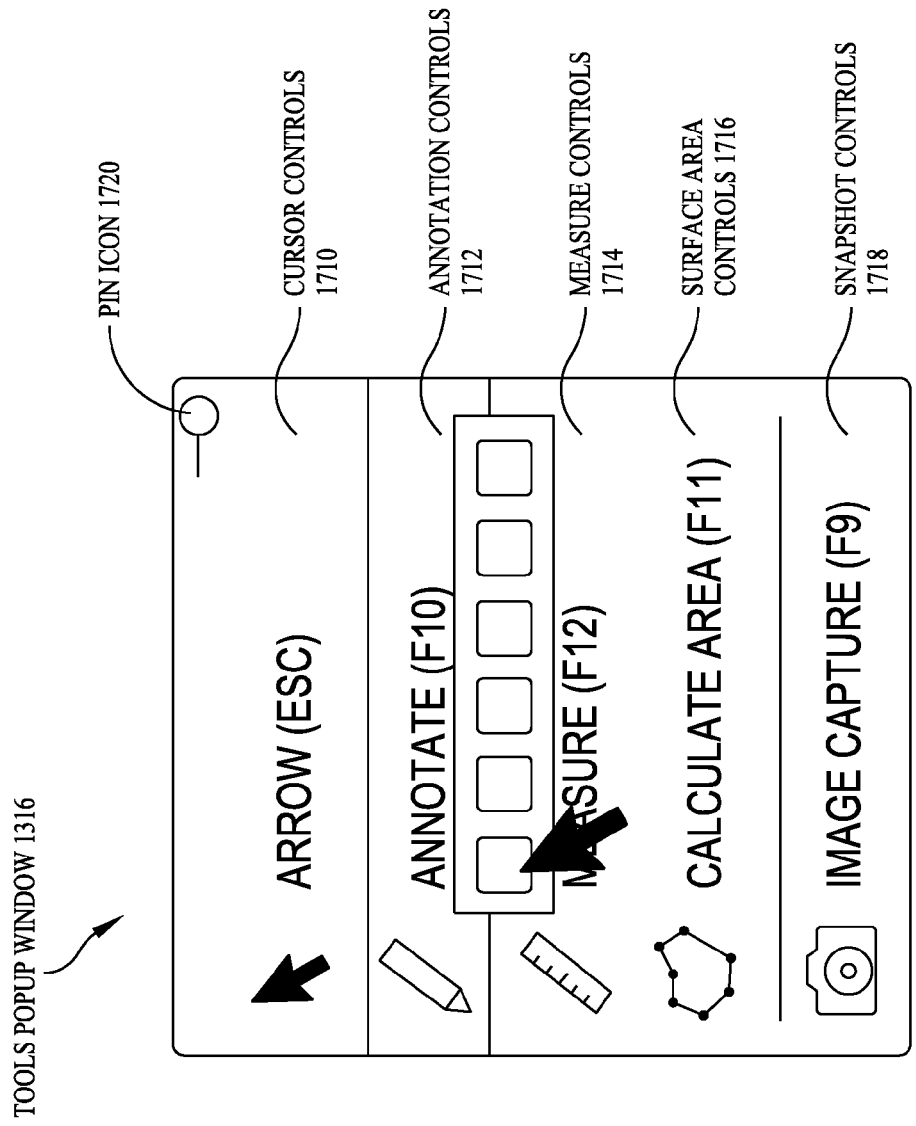
FIG. 17A shows details of a tools popup window of the viewer main menu of the digital pathology system.

FIG. 17A shows more details of tools popup window 1316 of viewer main menu 1300. Right clicking with mouse 436 anywhere in digital microscope viewing window 1310 may bring up tools popup window 1316 that contains tools and preferences. Tools popup window 1316 may include, but is not limited, to five sets of controls—cursor controls 1710, annotation controls 1712, measure controls 1714, surface area controls 1716, and snapshot controls 1718. Tools popup window 1316 may also have an option to set preferences. The tools of tools popup window 1316 may be used with mouse 436 (not with slide-navigation device 438).

Clicking a pin icon 1720 pins down tools popup window 1316 on digital microscope viewing window 1310. In this way, tools popup window 1316 becomes a toolbox. Clicking pin icon 1720 again causes tools popup window 1316 to disappear.

Cursor controls 1710 of tools popup window 1316 are used to select the appearance of the cursor. The standard cursor is the default tool. The standard cursor allows the user to click and drag to pan across the image. Because the other tools only apply to the slide image, when another tool is selected the system should temporarily switch back to the standard cursor when the user moves the mouse over slide tray viewing window 1312 or workflow main menu 500 at first display 428. However, the system should switch back to the selected tool as soon as mouse 436 moves back to the slide image.

When the user selects annotation controls 1712 of tools popup window 1316, the cursor changes to the shape of a pen and users 160 can make freehand drawings on the slide image by holding down the left mouse button. When the user 160 holds down the mouse over the annotation tool for a second, a submenu may appear that allows the user 160 to select the color of the annotation. Multiple marks made consecutively may be considered a single annotation by the system. For example, a pathologist may place dots on either side of a tumor and this set of dots should be considered a single annotation. The user can indicate that they are done making an annotation in several ways, such as, but not limited to, changing tools, changing the color of the annotation tool, pressing the escape key on the keyboard, and/or panning the image so that no parts of the annotation appear on the screen. After indicating that an annotation is complete, any marks made by the annotation tool are considered part of a new annotation. Other annotation markings are possible, such as superimposed geometric outlines in shapes that are selected by the pathologist and potentially are associated by the pathologist with some aspect or the image that has been noted.

Figure 17B:
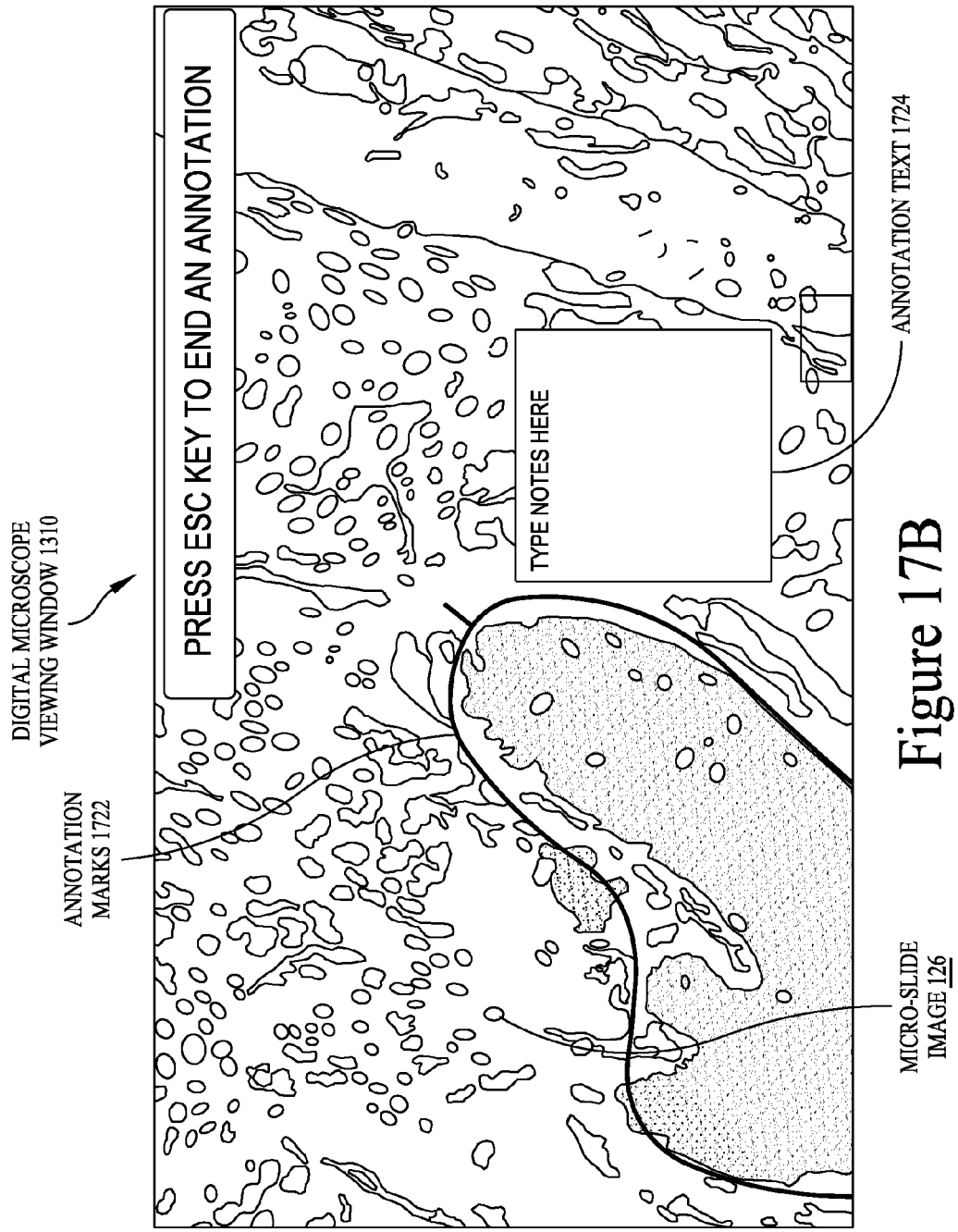
FIG. 17B shows annotation marks that may be formed by use of annotation controls of the viewer main menu of the digital pathology system.

By way of example, FIG. 17B shows annotation marks 1722 that may be formed by use of annotation controls 1712. Additionally, FIG. 17B shows annotation text 1724 that may be entered by user 160. All of the annotations made on the slide image may be toggled on and off using a keyboard shortcut or an icon on the status bar.

Figure 18A:
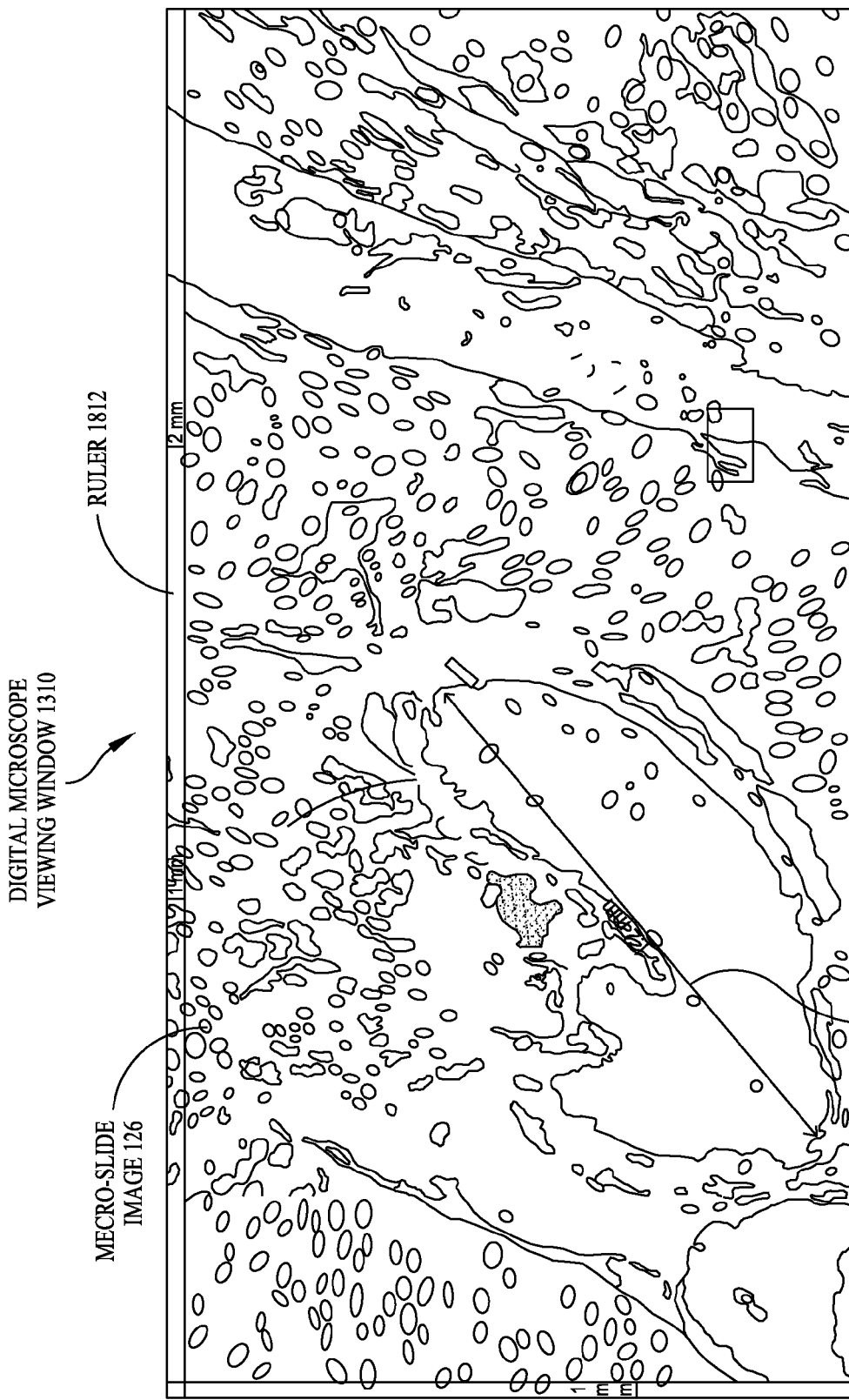
FIG. 18A shows a measurement taken using measure controls of the viewer main menu of the digital pathology system.

Measure controls 1714 of tools popup window 1316 are used by user 160 to measure the length of a line form, for example, by two left clicks of mouse 436 on the slide image. By way of example, FIG. 18A shows a measurement 1810, which is indicated by a line that is drawn between the locations of the two clicks of mouse 436. Text indicating the length of the line, taking into account the level of magnification to obtain a specimen-related measurement, appears next to the line. Multiple measuring tools can appear on the screen at once. All of the lines made using measure controls 1714 may be toggled on and off using a keyboard shortcut or the icon on the status bar. Lines created using measure controls 1714 can be deleted by right clicking on the line itself and choosing delete.

Figure 18B:
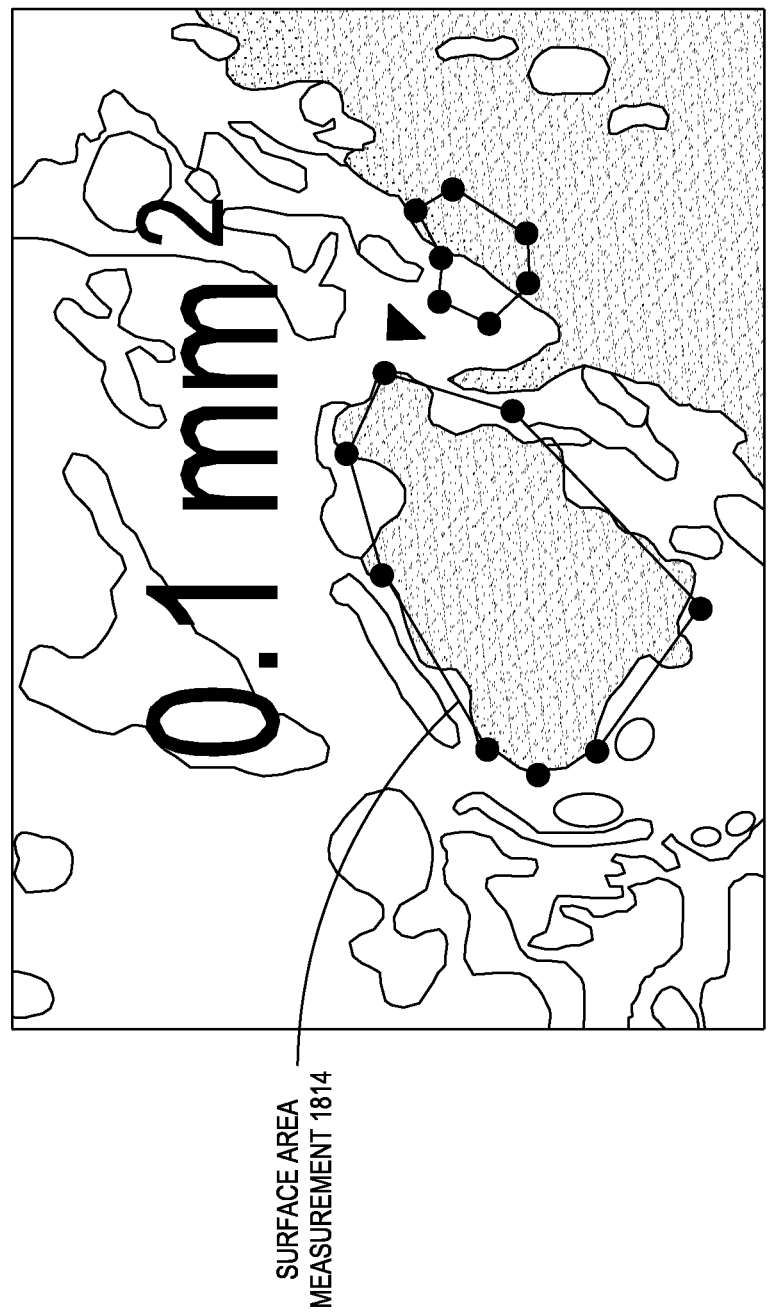
FIG. 18B shows a surface area measurement taken using surface area controls of the viewer main menu of the digital pathology system.

Referring again to FIG. 18A, an optional ruler 1812 may be displayed at the top and left edges of digital microscope viewing window 1310 for making measurement by comparison with the ruler. Surface area controls 1716 of tools popup window 1316 may be used to calculate the surface area between dots (e.g., forming a polygon) in digital microscope viewing window 1310. Once surface area controls 1716 are selected, clicking on the image will start a new surface area polygon. Once two additional clicks occur at different points along the image, a line is drawn around the points to create an area. Additional clicks add new vertices to this area. The line should connect the points in the order in which they were created. By way of example, FIG. 18B shows a surface area measurement 1814, which is indicated by a polygon that is drawn using the locations of the mouse clicks. Text appears next to the polygon indicating the size of the area inside the polygon. The user can indicate that they are done making a surface area by, for example, changing tools or pressing the escape key on the keyboard. Polygons created using surface area controls 1716 can be deleted by right clicking on the polygon itself and choosing delete.

Figure 19:
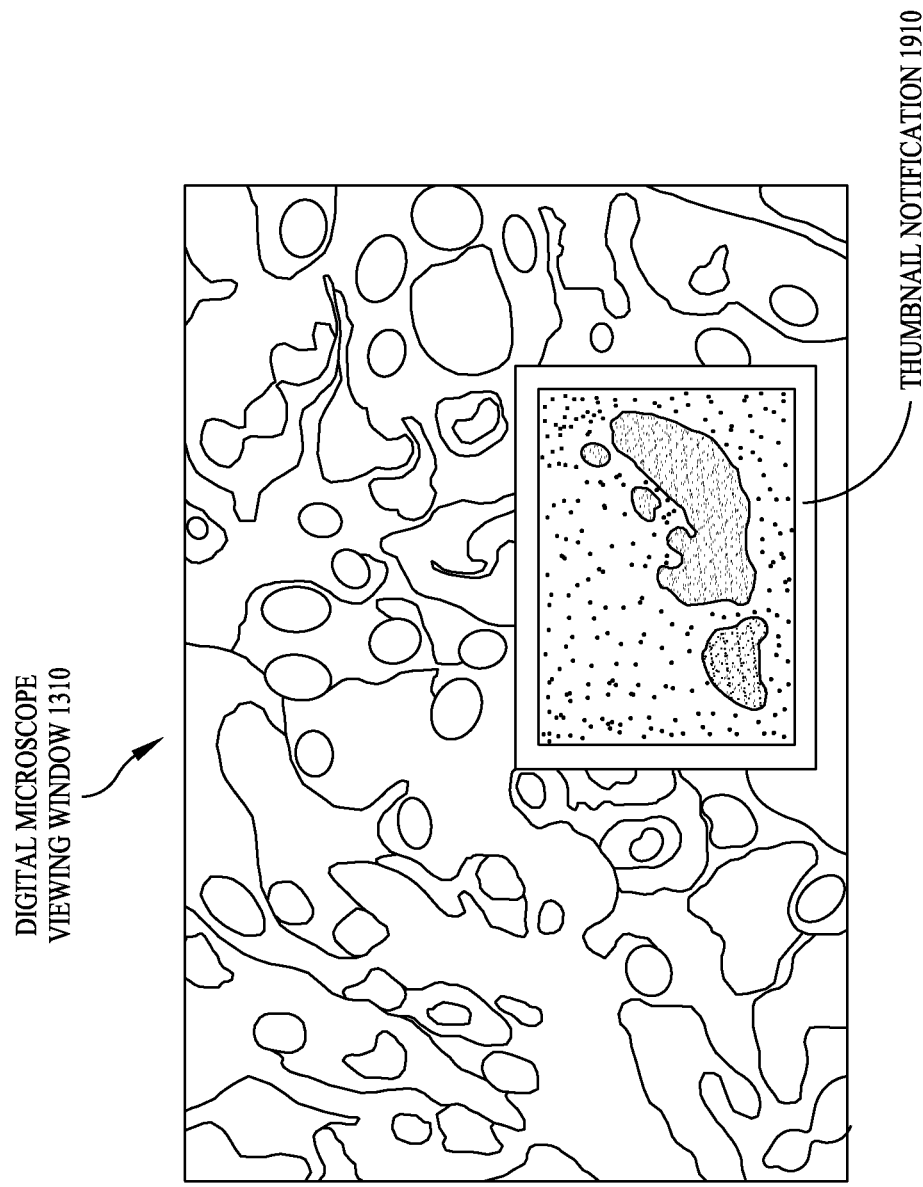
FIG. 19 shows a snapshot thumbnail that may appear in a digital microscope viewing window of the viewer main menu of the digital pathology system.

Using snapshot controls 1718 of tools popup window 1316, a screen capture may occur of the entire digital microscope viewing window 1310. The entire area of tissue visible in digital microscope viewing window 1310 is captured so that pathologists can be assured that the area of interest is captured by the snapshot. All snapshots get added to annotations and snapshots window 1322 of slide tray viewing window 1312 as soon as they are created. The snapshots are linked back to the corresponding part of the slide image. When a snapshot is triggered, an audible sound representing the sound of a shutter or the like may be played by digital pathology system 100 to signal that the action has been taken. In addition, a small notification with a thumbnail of the snapshot may appear in digital microscope viewing window 1310 and fade away after a few seconds. By way of example, FIG. 19 shows a thumbnail notification 1910, which is an example of a thumbnail of the snapshot that may appear in digital microscope viewing window 1310 and fade away after a few seconds.

Figure 20:
FIG. 20 shows a table of an example of keyboard shortcuts of the digital pathology system.

Digital pathology system 100 may support multiple versions of keyboard shortcuts. For example, a right hand version of keyboard shortcuts and two left hand versions of keyboard shortcuts. By way of example, FIG. 20 shows a table of an example of keyboard shortcuts 2000. The right hand version is intended for when slide-navigation device 438 is in the left hand, and assumes a typical desktop keyboard with a number pad on the right side of the keyboard. One left hand version involves a combination key for next and previous slide. An alternate hand version moves the next and previous slide commands to the function keys for pathologists who might wish to avoid the extra key press. Function keys (F1-F12) may be assigned for less frequent and more consequential actions.

Under the control of user state component 220 of DPA services 112 of workflow server 110, digital pathology system 100 provides the ability to switch between multiple cases while preserving the state of each case at the time of the switch with respect to what the user 160 last viewed via workflow main menu 500 at first display 428 and viewer main menu 1300 at second display 430. An example of viewing multiple cases simultaneously and preserving the current views is illustrated with respect to FIGS. 21A and 21B, 22A and 22B, and 23A and 23B.

Figure 21A:
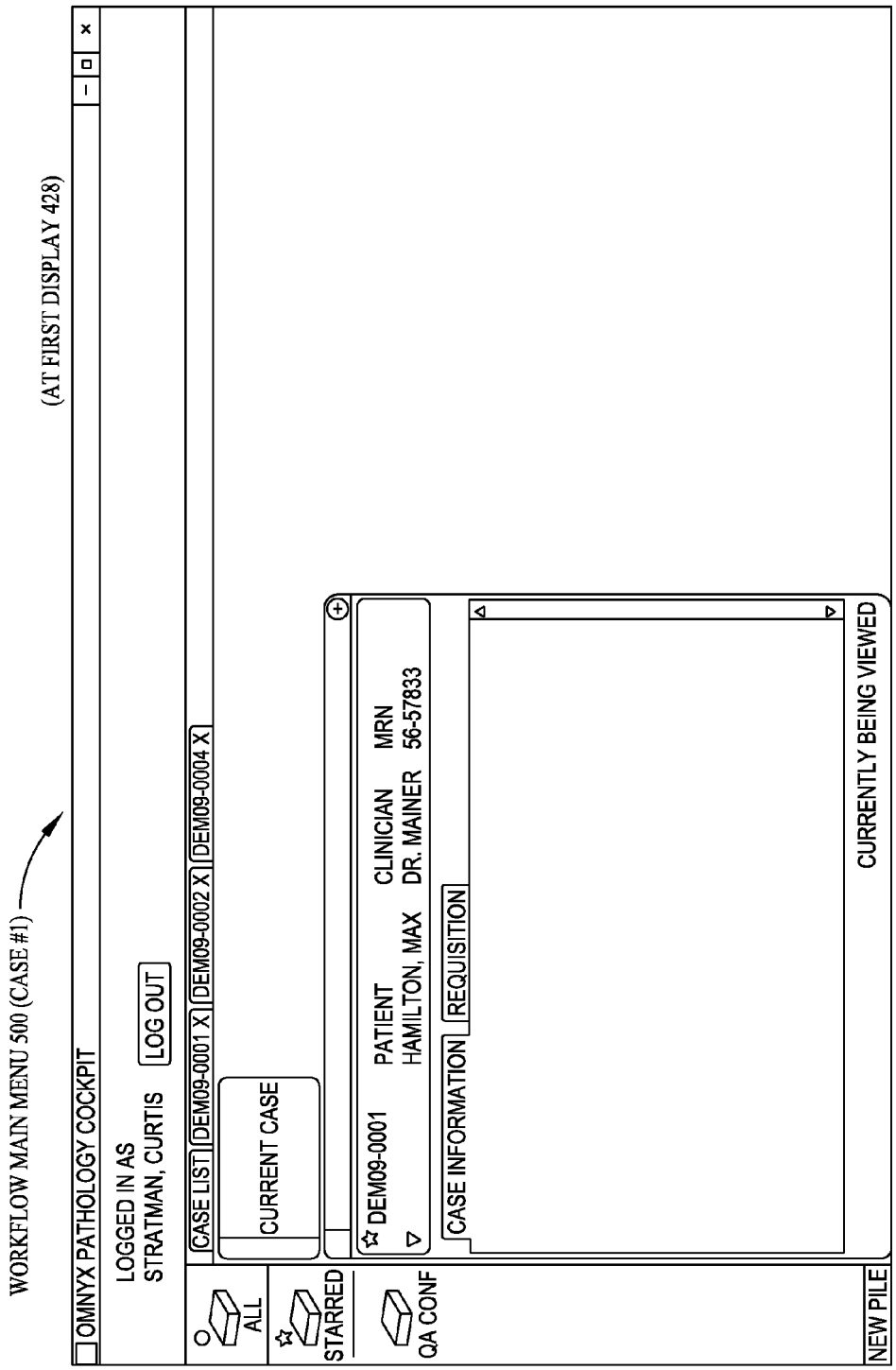
FIGS. 21A and 21B, 22A and 22B, and 23A and 23B illustrate an example of viewing multiple cases simultaneously and preserving the current views when switching between cases.
Figure 21B:
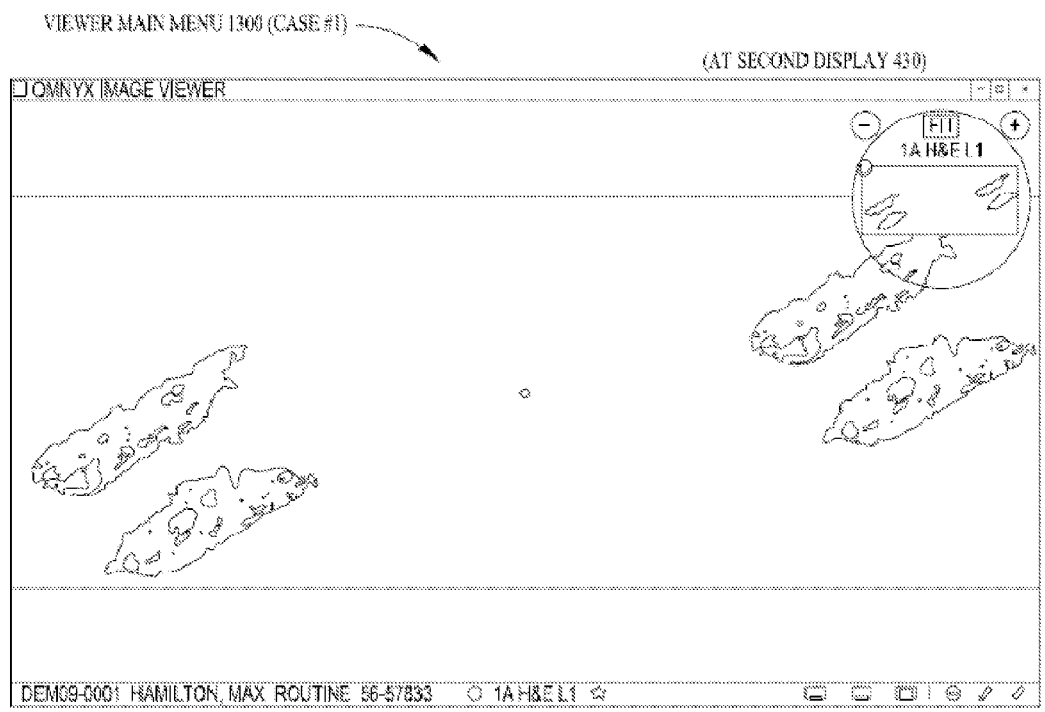

For a case #1, FIGS. 21A and 21B show the saved views of workflow main menu 500 at first display 428 and viewer main menu 1300 at second display 430, respectively. Workflow main menu 500 shows that three cases are open (i.e., three case tabs 722). However, in these views a DEM09-0001 case tab 722 of workflow main menu 500, which corresponds to case #1, is the active tab. Also, the color code of the "Current Case" selection box 1016 is "blue" to indicate ROUTINE priority. Additionally, an image of a slide 716 that is specific to case #1 is shown in viewer main menu 1300.

Figure 22A:
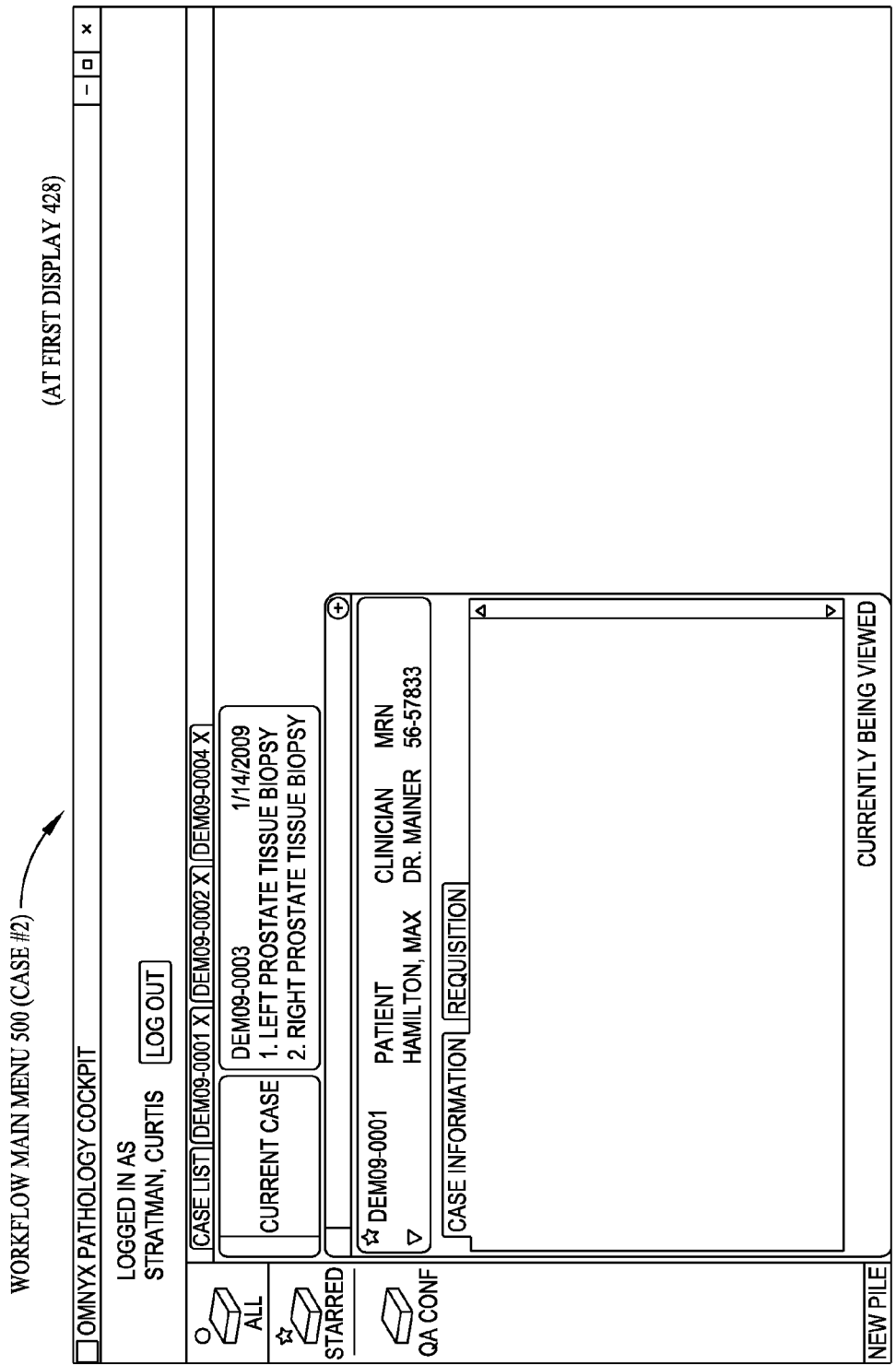
Figure 22B:
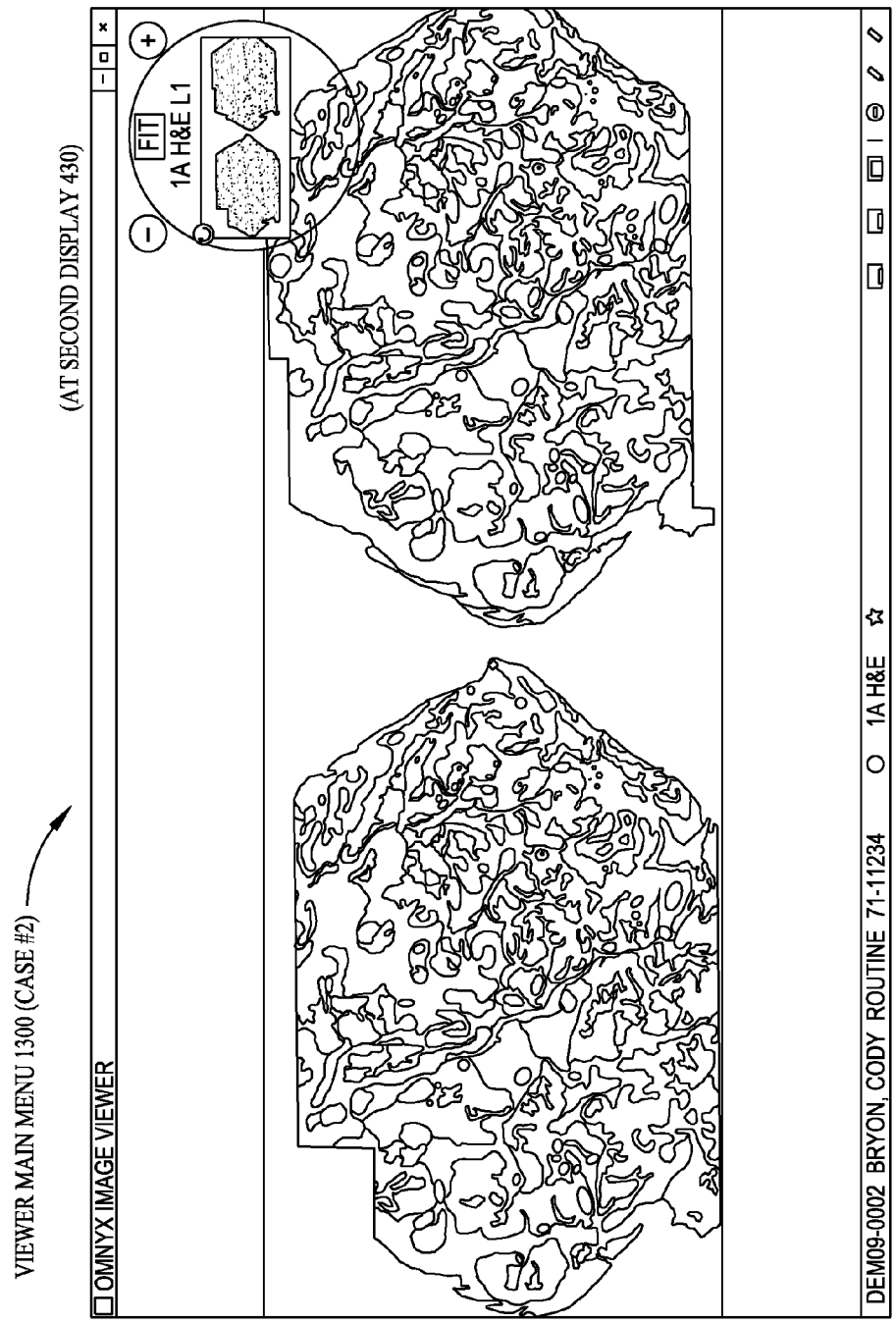

For a case #2, FIGS. 22A and 22B show the saved views of workflow main menu 500 at first display 428 and viewer main menu 1300 at second display 430, respectively. Again, workflow main menu 500 shows that three cases are open (i.e., three case tabs 722). However, in these views a DEM09-0002 case tab 722 of workflow main menu 500, which corresponds to case #2, is the active tab. Also, the color code of the "Current Case" selection box 1016 is "blue" to indicate ROUTINE priority. A "Past Case" selection box 1016 is also shown. Additionally, an image of a slide 716 that is specific to case #2 is shown in viewer main menu 1300.

Figure 23A:
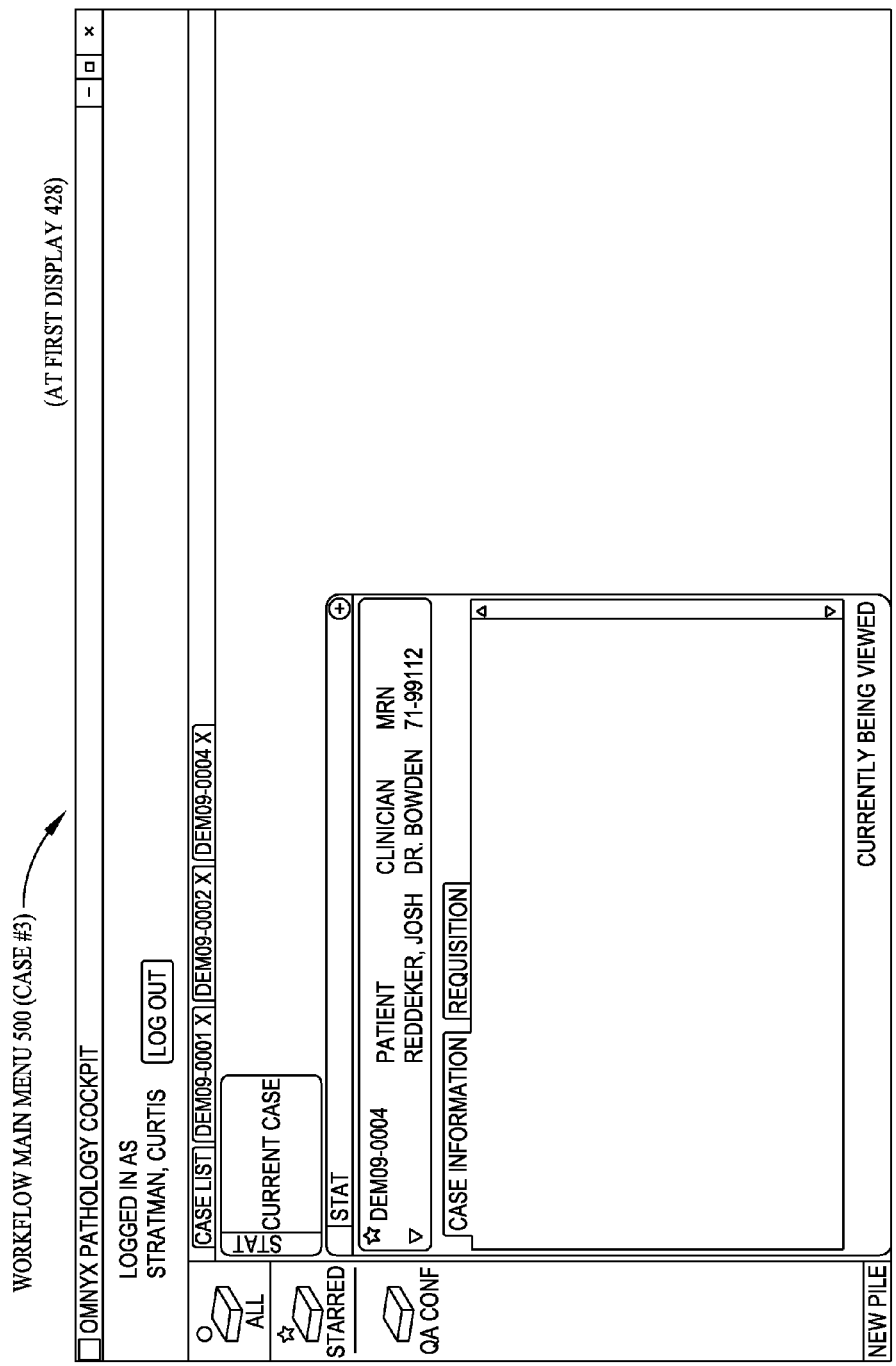
Figure 23B:
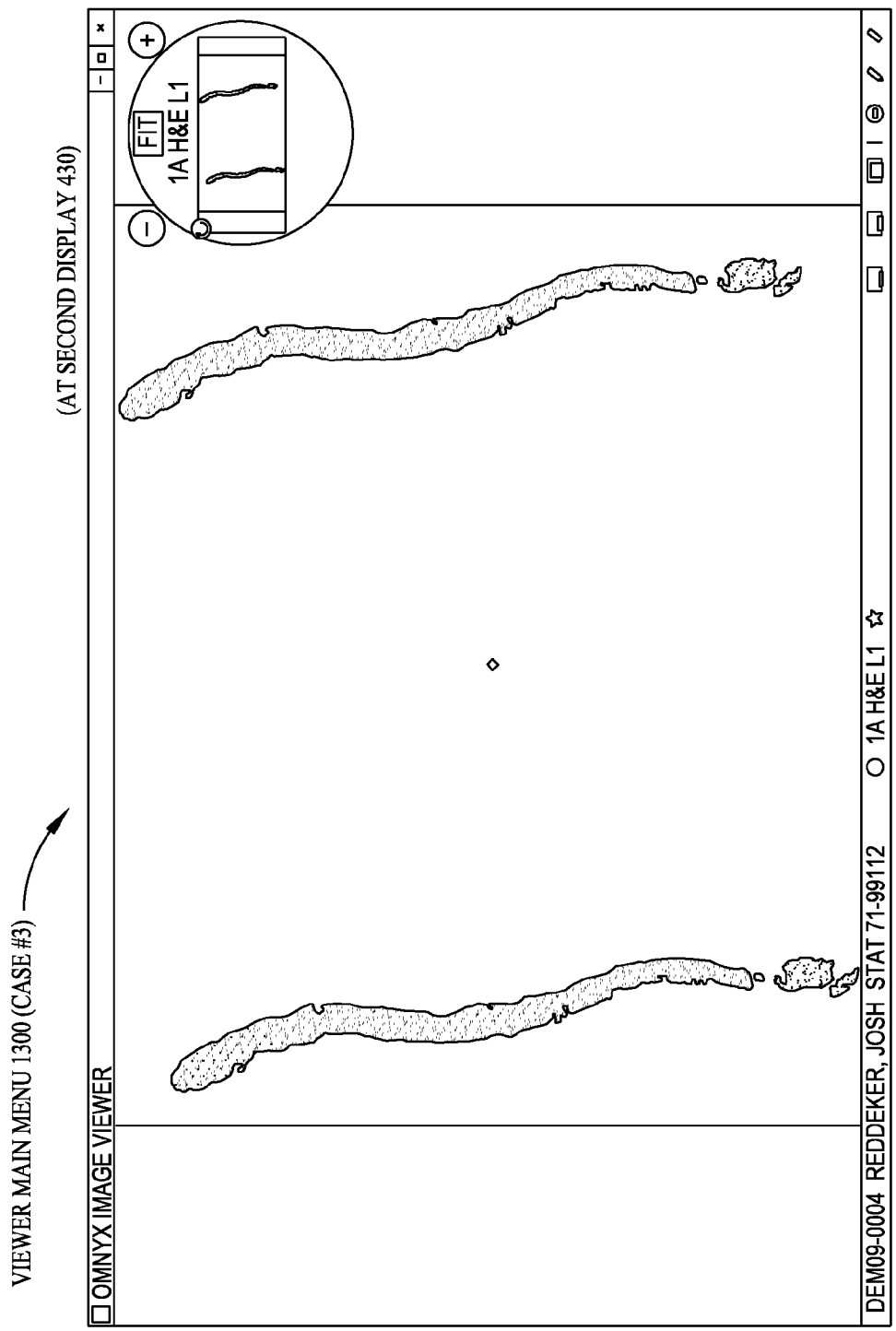

For a case #3, FIGS. 23A and 23B show the saved views of workflow main menu 500 at first display 428 and viewer main menu 1300 at second display 430, respectively. Again, workflow main menu 500 shows that three cases are open (i.e., three case tabs 722). However, in these views a DEM09-0004 case tab 722 of workflow main menu 500, which corresponds to case #3, is the active tab. Also, the color code of the "Current Case" selection box 1016 is "red" to indicate STAT priority. Additionally, an image of a slide 716 that is specific to case #3 is shown in viewer main menu 1300.

Referring again to FIGS. 13 through 23A, the graphical menus shown therein are exemplary only of viewer menus 426 of viewer module 422 of DPA client 138 of each pathology workstation 118. The menus shown in FIGS. 13 through 23A are not meant to be limiting, any other menu designs that, preferably, attempt to resemble and/or mimic physical pathology systems and processes are possible.

Figure 24A:
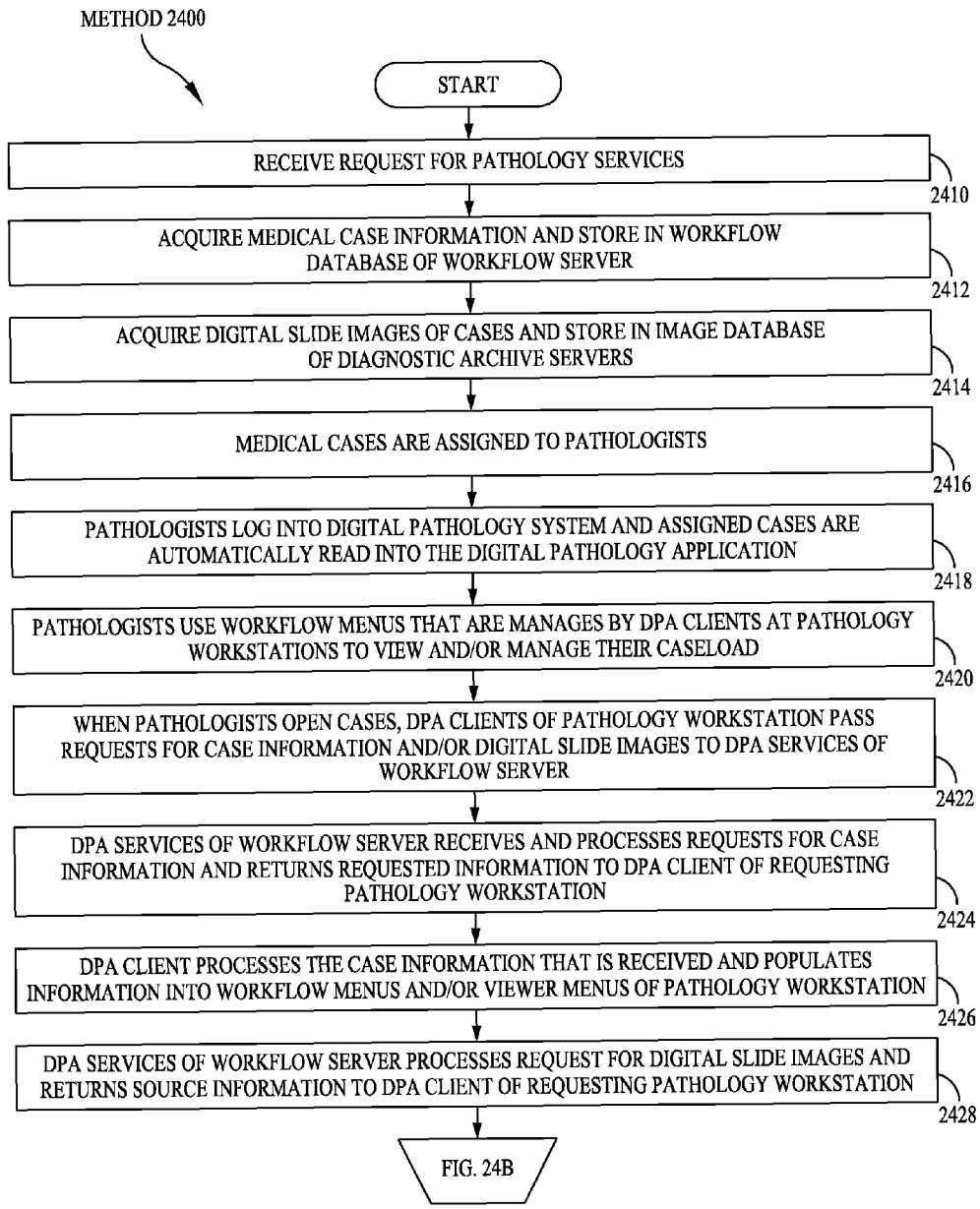
FIGS. 24A and 24B illustrate a flow diagram of a method of operation and/or use of the digital pathology system.
Figure 24B:
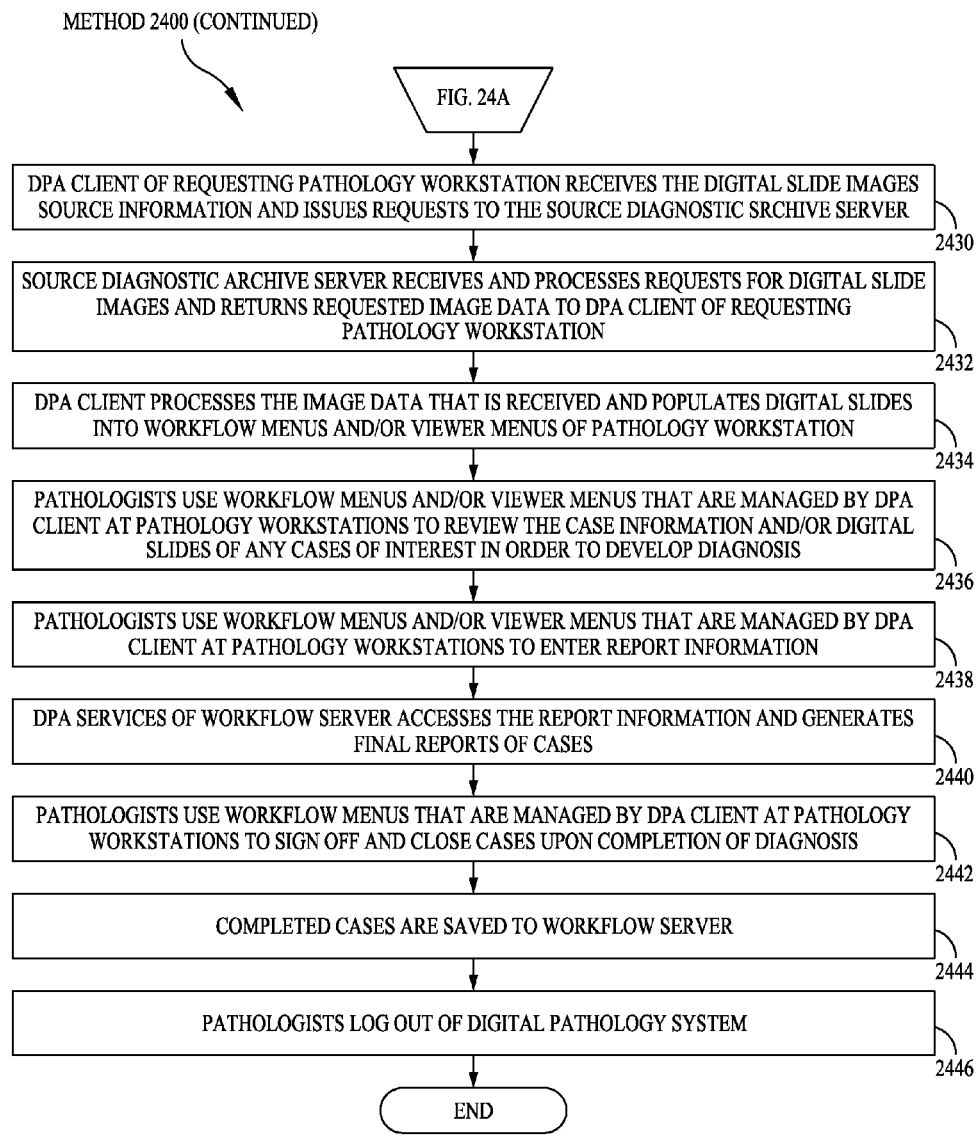

FIGS. 24A and 24B illustrate a flow diagram of a method 2400 of operation and/or use of digital pathology system 100. FIGS. 1 through 23B of digital pathology system 100 may be referenced throughout the steps of method 2400. Method 2400 may include, but is not limited to, the following steps, which may be implemented in any order.

At step 2410, requests for pathology services are received at digital pathology system 100. For example, requests for pathology services may originate from third party servers 120 within by transmitting third party data 142 to DPA services 112 at workflow server 110. More specifically, requisition sheets may be included in third party data 142 for processing at workflow server 110.

At step 2412, the medical case information that is acquired may be stored in workflow database 136 of workflow server 110. For example, the medical case information that is included in third party data 142 from third party servers 120 may be stored in case data 244 of workflow database 136 of workflow server 110.

At step 2414, digital slide images of cases are acquired and stored in image database 122 of diagnostic archive servers 116. For example, physical glass slides 132 of medical cases may be scanned by scanners 130 at diagnostic archive servers 116, in this way the physical glass slides 132 are digitized in a manner that is suitable for use in digital pathology system 100. More specifically, macro-slide images 124 and/or micro-slide images 126 that are associated with physical glass slides 132 are created by scanners 130 and stored in image database 122. In particular, content services 128 of diagnostic archive servers 116 are used to manage inbound image data that is received from scanners 130.

At step 2416, medical cases are assigned to pathologists. For example, an administrator of digital pathology system 100 may assign cases to certain users 160. This process may be managed by use of administrator component 212 of DPA services 112 at workflow server 110.

At step 2418, pathologists (i.e., users 160) log into digital pathology system 100 and the assigned cases are automatically read into the digital pathology application. For example, a certain pathologist (i.e., user 160) may access workflow menus 424 of DPA client 138 at his/her respective pathology workstation 118 and log into digital pathology system 100. Upon successful login, the assigned cases are automatically read into workflow menus 424 and/or viewer menus 426. More specifically, the assigned cases are automatically read into piles view window 512 of workflow main menu 500. The login process may be managed by authentication component 210 of DPA services 112 at workflow server 110. Authentication component 210 may access, for example, system data 240 and/or user data 242 in workflow database 136 in order to authenticate the user 160.

At step 2420, pathologists use workflow menus 424 that are managed by DPA client 138 at pathology workstations 118 to view and/or manage their caseload. For example, pathologists may use piles view window 512 of workflow main menu 500 to view and/or manage their caseload.

At step 2422, when pathologists open cases, DPA client 138 at pathology workstations 118 pass requests for case information and/or digital slide images to DPA services 112 of workflow server 110.

At step 2424, DPA services 112 of workflow server 110 receives and processes the requests for case information and returns the requested information to DPA client 138 of the requesting pathology workstation 118. For example, case assembly component 214 of DPA services 112 of workflow server 110 accesses case data 244 in workflow database 136 and returns the requested case information to the requesting pathology workstation 118.

At step 2426, DPA client 138 of the requesting pathology workstation 118 processes the case information that is received and populates the information into workflow menus 424 at first display 428 and/or viewer menus 426 at second display 430 of pathology workstation 118.

At step 2428, DPA services 112 of workflow server 110 processes requests for digital slide images and returns the source information to DPA client 138 of the requesting pathology workstation 118. For example, case assembly component 214 of DPA services 112 of workflow server 110 may be used to query image catalog data 246 in workflow database 136 and determine the diagnostic archive server 116 that is the source of the requested digital slide images. Once the source diagnostic archive server 116 has been determined, DPA services 112 of workflow server 110 returns the path to DPA client 138 of the requesting pathology workstation 118.

At step 2430, DPA client 138 of the requesting pathology workstation 118 receives the source information from DPA services 112 of workflow server 110 and issues requests to the source diagnostic archive server 116 for the digital slide images of interest (e.g., macro-slide images 124 and/or micro-slide images 126 of interest).

At step 2432, the source diagnostic archive server 116 receives and processes requests for digital slide images and returns the requested image data to DPA client 138 of the requesting pathology workstation 118. In particular, streaming services 134 of diagnostic archive servers 116 is used to manage outbound image data that is transmitted to any entity that is connected to network 114 of digital pathology system 100. Additionally, the transmission of image data over network 114 is minimized by transmitting only portions of a digital slide image that is being viewed at the time, i.e., streaming services 134 supports a just-in-time viewing feature. In this way, the network data bandwidth requirements and performance of the system are optimized.

At step 2434, DPA client 138 of the requesting pathology workstation 118 processes the image data that is received from the source diagnostic archive server 116 and populates digital slides (e.g., slides 716) into workflow menus 424 at first display 428 and/or viewer menus 426 at second display 430 of pathology workstation 118.

At step 2436, pathologists use workflow menus 424 at first display 428 and/or viewer menus 426 at second display 430 that are managed by DPA client 138 at pathology workstations 118 to review the case information and/or slides 716 of any cases of interest in order to develop diagnoses. For example, pathologists use workflow main menu 500 and any associated menus that are described in FIGS. 5 through 12, as well as viewer main menu 1300 and any associated menus that are described in FIGS. 13 through 20, to review the case information and/or slides 716 of any cases of interest in order to develop diagnoses.

Continuing step 2436, pathologists may be reviewing multiple cases simultaneously. In this case, user state component 220 of DPA services 112 of workflow server 110 provides the ability to switch between multiple cases while preserving the state of each case at the time of the switch with respect to what the user 160 last viewed via workflow main menu 500 at first display 428 and viewer main menu 1300 at second display 430. An example of viewing multiple cases simultaneously and preserving the current views is illustrated with respect to FIGS. 21A and 21B, 22A and 22B, and 23A and 23B.

At step 2438, pathologists use workflow menus 424 at first display 428 and/or viewer menus 426 at second display 430 that are managed by DPA client 138 at pathology workstations 118 to enter report information. For example, in the process of reviewing cases, pathologists may access a "Report" selection box 1016 of case detail page 1010 of workflow main menu 500. In doing so, a text entry window may be presents in, second panel 1014 of case detail page 1010, such as shown in FIG. 10A. The pathologist may then enter any information to be integrated into a final report of the case.

At step 2440, DPA services 112 of workflow server 110 accesses the report information that is entered into case detail page 1010 of workflow main menu 500 and generates final reports of cases. Reporting mechanisms advantageously can be permitted to vary from one hospital to another by providing report formatting capability or a selection among a set of alternative pre-formatted reports. Therefore, reporting component 224 of DPA services 112 may be used to integrate the report information into any reporting mechanism by converting the content to any file format and/or data entry system.

At step 2442, upon completing a diagnosis of a case, pathologists use workflow menus 424 at first display 428 and/or viewer menus 426 at second display 430 that are managed by DPA client 138 at pathology workstations 118 to sign off and close cases.

At step 2444, completed case information is saved to case data 244 of workflow database 136 of workflow server 110. In doing so, the case information is accessible by any interested entities that are connected to network 114 of digital pathology system 100.

At step 2446, pathologists log out of digital pathology system 100. For example, pathologists log out of digital pathology system 100 by clicking a log out pushbutton 511 provided for that purpose on workflow main menu 500.

Figure 25:
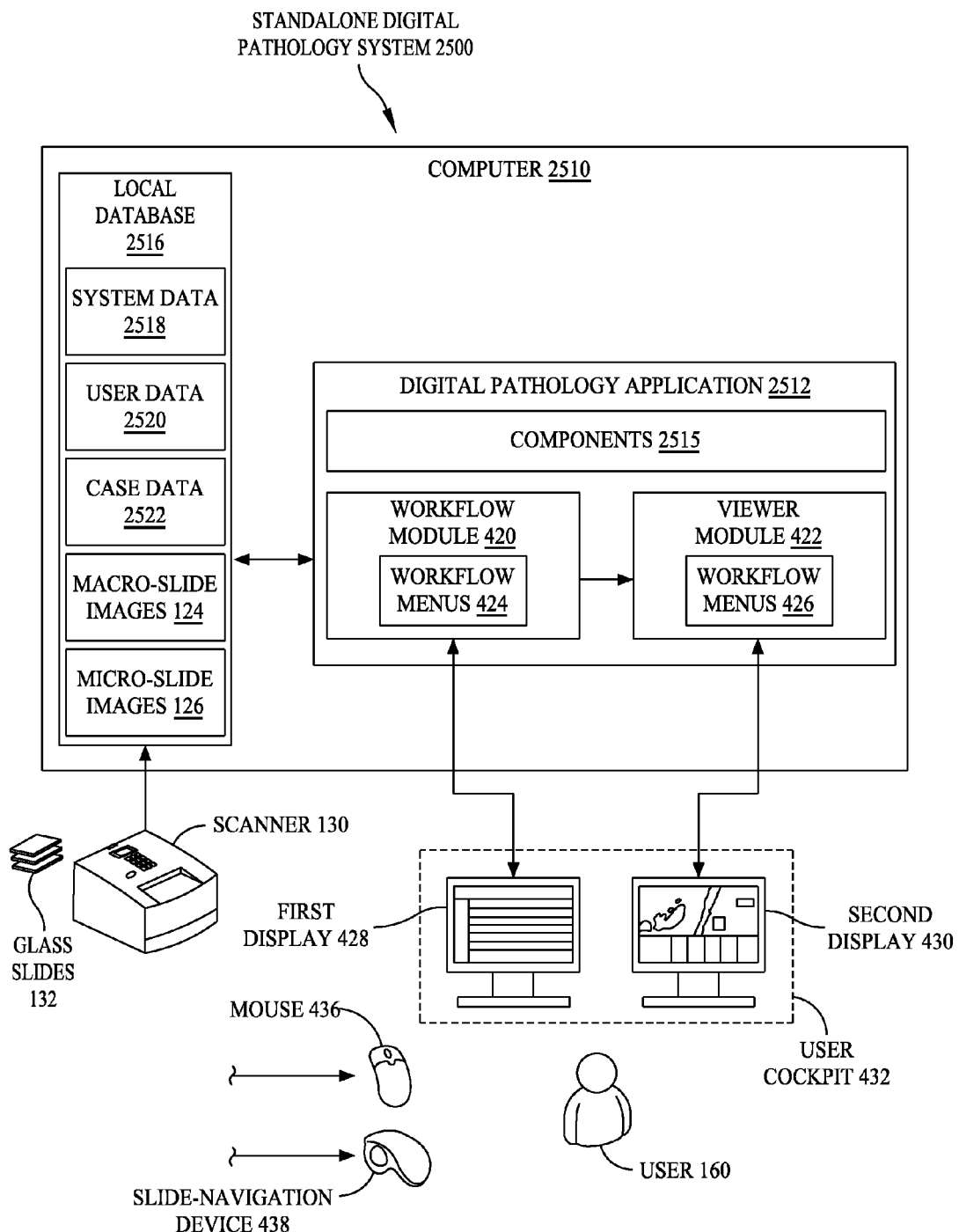
FIG. 25 illustrates functional block diagram of an example of a standalone digital pathology system.

FIG. 25 illustrates functional block diagram of an example of a standalone digital pathology system 2500. Standalone digital pathology system 2500 provides substantially the same functionality of digital pathology system 100 of FIGS. 1 through 4. However, the functionality of standalone digital pathology system 2500 is implemented in a substantially autonomous standalone configuration, rather than with the distributed functionality of a networked configuration.

Standalone digital pathology system 2500 may include a computer 2510, which may be any substantially standalone computing device, such as, but not limited to, a laptop, desktop, or handheld computer. Residing at and executing on computer 2510 may be a digital pathology application 2512 the further includes certain software components 2514. Digital pathology application 2512 may provide substantially the same functionality as the combination of DPA services 112 at workflow server 110 and DPA client 138 at each pathology workstation 118 of digital pathology system 100, albeit without the networking aspects. In particular, software components 2514 may provide substantially the same functionality as the components shown in FIG. 2 of DPA services 112 at workflow server 110, albeit without the networking aspects.

Digital pathology application 2512 of computer 2510 may also include workflow module 420 that manages workflow menus 424 and viewer module 422 that manages viewer menus 426, as described with reference to digital pathology system 100 of FIGS. 4 through 24. Further, workflow module 420 manages first display 428 and viewer module 422 manages second display 430, again as described with reference to FIGS. 4 through 24. Computer 2510 also includes mouse 436 and slide-navigation device 438, which are the dual input devices that are described with reference to FIGS. 4 through 24.

Computer 2510 also includes a local database 2516. Local database 2516 may provide substantially the same functionality as the combination of workflow database 136 of workflow server 110, image database 122 of diagnostic archive servers 116, and memory 442 of client computers 440 of pathology workstations 118, as described with reference to digital pathology system 100 of FIGS. 4 through 24. For example, stored in local database 2516 may be system data 2518, which substantially corresponds to system data 240 of workflow database 136; user data 2520, which substantially corresponds to user data 242 of workflow database 136; case data 2522, which substantially corresponds to case data 244 of workflow database 136; as well as a collection of macro-slide images 124 and/or micro-slide images 126, which substantially correspond to the image data of image database 122. FIG. 25 shows that one or more scanners 130, which are the source of macro-slide images 124 and/or micro-slide images 126, are connected directly to computer 2510.

Network connectivity may be required standalone digital pathology system 2500 for the initial acquisition of data, such as user data 2520 and/or case data 2522, which may include data from a third party (e.g., third party data 142 from third party servers 120). Network connectivity may not be required for the acquisition of macro-slide images 124 and/or micro-slide images 126 because there is at least one scanner 130 connected directly to computer 2510. However, once all the necessary information has been acquired and stored in local database 2516, standalone digital pathology system 2500 may be operated autonomously by a certain user 160 (e.g., a pathologist) to process case information and digital slide images in order to form their diagnoses using workflow menus 424 and viewer menus 426, as described with reference to digital pathology system 100 of FIGS. 4 through 24.

In summary and referring to FIGS. 1 through 25, digital pathology system 100 and method 2400 of the present disclosure provide the combination of workflow menus 424 and viewer menus 426 to provide a hierarchy of visual elements that substantially resemble and/or mimic the hierarchy of elements in prior art physical pathology instrumentation. Further, digital pathology system 100 and method 2400 of the present disclosure provide an improved digital slide viewer function via workflow menus 424 and viewer menus 426 that may substantially resemble and/or mimic the slide navigation tools and features that are familiar to pathologists who have used prior art microscope systems, thereby continuing to promote skill and expertise in a manner similar to the use of manual microscope systems.

The data processing system of digital pathology system 100 handles images of specimens and associated data using a source of digital image data representing images of the specimens to a predetermined magnification, preferably including an automated slide scanning system with associated controls including labels provided on the slides for automatic data capture, ensuring that the slide images are associated through processing with the case packages to which they belong. An image database has memory storing the digital image data and associated data relating to the image data and a workflow database has memory storing case management data associated with the specimens. The computer workstation, including at least one digital processor coupled to the image database and to the workflow database, is programmed and responsive to user control, to obtain and display selected ones of the images for review, to accept user input and to record in at least one of the image database and the workflow database information resulting from the user input. The programmed processor presents the image data to the user at the workstation, on a display controlled according to the user input to emulate controls of an optical microscope, and according to a workflow or sequence of operations for microscopic viewing and one or more of histological, cytological and pathological study and reporting upon tissue samples associated with patient case files.

The patient case files can have images of one or more tissue samples and specimen slides. Each specimen slide can have plural image views stored in the image database for diverse locations, diverse levels of magnification, alternative stains or treatments, etc. The image database and in the workflow database can contain case packages for multiple institutions, numerous users and even more numerous patients. The case packages can be related based on one or more variable values stored in the databases. During display of a case package, the user can be provided options to manipulate the case packages in the manner described above, and also to selectively switch to presentation of one or more other case packages that may be related, for example, as being an earlier case package concerning the same patient, and potentially also the same body part or block. The system and methods as disclosed thus enable organized presentation for comparison of images and data at successive stages in the progress of the patient over time. The information may be partly archived but remains conveniently organized and accessible by accessing the database. Instead of handling slides, files and paper copies of documents and images, the user can handle a given case package, and also review any previously processed case packages of the same patient, whether or not reviewed by the same user, to compare the case packages and monitor changes occurring in sequence over a period of time.

The invention has been described with respect to a number of objects and aspects, and explained with reference to preferred arrangements, possible alternatives and other examples. However the invention is not limited to the embodiments given as examples. Reference should be made to the appended claims and not the foregoing discussion of exemplary embodiments, to assess the scope of the invention in which exclusive rights are claimed.

We claim:

1. A data processing system for aid of a medical pathologist in manual workflow involving review, analysis and reporting on patient case information that includes microscopic images of patient tissue specimens and associated data, comprising:

a source of digital image data representing images of the patient tissue specimens to a plurality of predetermined magnifications for plural patients including cases to be reviewed by the pathologist;

an image database containing memory for storing the digital image data and associated data relating to the image data;

a workflow database containing memory for storing case management data associated with examination of the specimens by the pathologist;

a computer workstation comprising at least one digital processor coupled to the image database and to the workflow database, the processor being operable under control of a user to obtain and display selected ones of the images for review, to accept user input from the pathologist relating to the examination of the specimens by the pathologist and to record in at least one of the image database and the workflow database information resulting from the user input;

wherein the digital processor is programmed, in conjunction with display of the image data, to present to the user a display based on the case management data in the workflow database, said display comprising visual representations emulating contents of physical case packages that include paper files and glass slides forming workload units to be reviewed, wherein the processor is programmed to select and to display digital image data obtained from the physical case packages upon user selection and manipulation of display icons that graphically represent depictions of the physical case packages and depictions of the glass slides, said emulating including visually representing the case packages and the glass slides as icons that are visibly changed in at least one of a shape, size, orientation, color, blinking characteristic, animation characteristic and position of the icons in a user display for manipulating the case management data in the workflow database to virtually correspond with user handling of physical case packages and the glass slides;

wherein the processor is operable when accessing at least one of the image database and the workflow database, to associate the images with digital document data relating to the case package and its associated patient.

2. The data processing system of claim 1, wherein the handling comprises selecting and organizing case packages and steps in a predetermined sequence for diagnostic microscopic viewing and reporting on the case packages by the pathologist via the workstation, upon tissue samples associated with patient case files, wherein each of said patient case files has images of one or more tissue samples and specimen slides, wherein each said specimen slide has plural image views stored in the image database and the views are selectable by the pathologist controlling the workstation to select among the case packages via the workstation and to present selected locations on slides in the case packages on the user display at selected levels of magnification.

3. The data processing system of claim 2, wherein the images comprise all viewable locations on the specimens on the slides to the predetermined magnification; wherein the processor is programmed to display to the user a location selected by the user; and wherein the processor is operable for fetching and processing from the image database, and for displaying to the user an image at the selected location and level of magnification selected by the user.

4. The data processing system of claim 2, wherein the image views selectable by the pathologist via the workstation include a substantially full scale view of a slide including a label, the label defining a changeable orientation of the slide, and one or more slides in a case package being reoriented by the processor and selection by the user of an input to indicate passing a step in a workflow.

5. The data processing system of claim 4, wherein the digital processor is programmed to present the image data to the user on a display under user operated inputs, for emulating use of an optical microscope by selection of a viewing location on a specimen mounted on a slide and selecting a magnification.

6. The data processing system of claim 2, wherein the information resulting from the user input comprises location information and annotations on the image at the selected location, and is stored in the image database.

7. The data processing system of claim 6, wherein the processor is operable when accessing at least one of the image database and the workflow database, to associate images and data from information on a slide label, information on one of a stored document and a stored document image, a stored medical image, a gross specimen image and information relating to one of a case package and an associated patient, wherein the processor is further operable to revert to display of selected ones of said images and said information due to an association with at least one of said information of the document, document image, medical image, gross specimen image, case package and patient.

8. The data processing system of claim 6, wherein the information resulting from the user input comprises case management information including selections generated by the user in preparation to view the images and status information generated by the digital processor reflecting progress in completion of the steps in the predetermined sequence, and wherein said case management information is stored by the digital processor in the workflow database.

9. The data processing system of claim 2, wherein the digital processor is programmed to associate data in the image database and in the workflow database for plural case packages that are related based on at least one variable value stored in one of the image database and the workflow database, and to present during presentation of one of said plural case packages, an option to switch to presentation of at least one other of the case packages that are related, whereby a user can select the option to compare said related case packages.

10. The data processing system of claim 9, wherein the plural case packages are related as case packages of at least one of a same patient, a same body part, a same block, a same pathological condition, and review by a same user.

11. The data processing system of claim 9, wherein the plural case packages are related as case packages of a same patient, and wherein the digital processor is programmed to sort the plural case packages in a time sequence, whereby the user can compare the case packages for changes occurring over the time sequence.

12. The data processing system of claim 1, wherein the digital processor is programmed to present at least one display based on said case management data, wherein at least one representation of a slide in the case package is a distinct place holder representation of a slide that has been identified as prospectively expected or as formerly available, but for which at least one form of image is not presently available for viewing.

13. The data processing system of claim 1, wherein the information resulting from the user input comprises case management information including selections generated by the user in preparation to view the images and status information generated by the digital processor reflecting progress in completion of the steps in the predetermined sequence; wherein said case management information is stored by the digital processor in the workflow database; and wherein the digital processor is programmed to generate displays selected by the user input representing parts of the case management information, the status information and the working information, for managing operations related to plural said slides and plural said case packages.

14. The data processing system of claim 13, wherein said displays selected by the user input include a display of a selected one of the case packages, together with associated slide images, that are selected from one of the image database and the workflow database, due to a relationship with at least one of a currently active case package, currently active slide image, current annotation, currently displayed information and currently displayed document, according at least one variable value stored in the workflow database.

15. The data processing system of claim 14, wherein the processor is controllable by said user input to suspend operations on the currently active one of the case packages, slide images, annotations, information and related documents, to store in the workflow database a record of a current state of review of said currently active one, and to revert to the selected one of the case packages, slide images, annotations, information and related documents, and thereafter to return to the current state of review of said currently active one under control of said user input, whereby the user is able to maintain plural case packages in progress while switching to displays of other case packages that can be related to the currently active one or unrelated to the currently active one.

16. The data processing system of claim 1, wherein manipulation of the case package icons associated with the files and slides via the user input includes categorizing the case packages to define piles by selecting and grouping icons visually resembling files and icons visually resembling slides, and wherein case packages are added to and removed from the piles under control by user input and by operation of the processor.

17. The data processing system of claim 16, wherein the processor is programmed to identify at least one of a categorization of the case packages and a categorization of the slides, by altering at least one of a size, shape, color parameter, orientation and location of associated said icons.

18. The data processing system of claim 17, wherein said categorization of the case packages and slides within said case packages by the processor includes visually distinguishing the associated said icons in a display presented to a user so as to distinguish a reviewed and not-reviewed state of the case packages and the slides.

19. The method of claim 18, wherein the plural case packages are related as case packages of a same patient, and wherein the digital processor is programmed to sort the plural case packages in a time sequence, whereby the user can compare the case packages for changes in said same patient occurring over the time sequence.

20. The data processing system of claim 17, wherein the workstation comprises at least two distinct display areas respectively configured for display of image data, controlled by the user input to emulate the controls of an optical microscope, and for display of the case management information, controlled by at least one of a keyboard and location selecting device.

21. The data processing system of claim 20, wherein the at least two distinct display areas have differently configured manual controls for at least one of positioning, selecting and variably controlling and entering of information for emulating the controls of an optical microscope, and for display of the case management information.

22. The data processing system of claim 1, wherein the computer workstation is one of a plurality of workstations coupled over a network to at least one server, maintaining at least one said image database, at least one said workflow database and a medical information database, and wherein the workflow database and the image database are accessible to plural users, whereby the image data and the information resulting from the user input are useful for later reference, and further professional review.

23. A method for digitally managing selection, examination and reporting upon patient samples by manual operations of a human pathologist or technician user assisted by computational steps using at least one programmed digital processor, comprising:

obtaining tissue samples and preparing the samples on slides;

scanning and digitally encoding microscopic images of at least a predetermined area of the slides encompassing the tissue samples so as to enable display of images of the tissue at plural selectable magnifications;

associating data and images defining a pathology patient, a patient case, and a patient tissue sample, and storing digital data files representing the microscopic images in at least one database with associated information identifying the data and images and associated patient information, the images from the slides and the associated patient information defining a virtual case package containing digital images and digital information including the associated patient information;

presenting to the user a display interface that emulates a pathologist's physical case package containing papers and a set of tissue samples mounted on glass slides by visual presentation of digital icons graphically representing the case package on the display interface as a case package selectable from a pile of case packages, and digital icons graphically representing the digital images in the case package as slides selectable from a slide tray;

managing selection and presentation of the digital images and the digital information on the display interface by user manipulation of the digital icons, thereby emulating manipulation and microscopic examination of the slides by manipulation of the digital icons representing the slides, and emulating handling of the case package by revising the digital information during review of the digital images and the digital information during a workflow accomplished by the user;

making the digital images and the digital information accessible over a network to plural users of the network;

providing a workstation having a digital processor in data communication with the at least one database, at least one display and input devices arranged for manipulation by the user;

operating the digital processor under control of a stored data processing program to present to the user options for selection of case packages and portions of case packages forming a workload, displaying to the user on the workstation the images and information and recording and storing in the at least one database, data generated as a result of review of the images and information by the user.

24. The method of claim 23, further comprising recording annotations by the user connected to one of a slide image and one or more locations on a slide image, and storing data representing the annotations in the at least one database.

25. The method of claim 23, further comprising determining a dimension defined by a plurality of said locations.

26. The method of claim 25, comprising associating one of said locations with the data generated as said result of the images and information by the user, and further comprising reverting to display of one of images and data upon encountering a user input selection and a workflow step associated with the one of said locations.

27. The method of claim 23, wherein the presentation and manipulation of images as controlled by the processor and as advanced by user input defines a workflow having at least certain predetermined steps including a concluding step selectable by the user.

28. The method of claim 27, wherein the workflow comprises a step of validating slides presented as constituting a patient sample by displaying slide icons and slide images for comparison with respect to attributes including at least one of tissue shape, size, color, character and associated information.

29. The method of claim 23, comprising associating plural case packages in the database based on a relationship of at least one variable value stored therein, presenting to a user of the workstation an option during presentation of one of said plural case packages to switch to presentation of at least one other of the case packages that is related to said one, and upon selection of said option to permit the user to compare said related case packages.

30. The method of claim 29, wherein the plural case packages are related as case packages of at least one of a same patient, a same body part, a same block, a same pathological condition, and review by a same user.

31. The method of claim 23, wherein said presentation and manipulation of the case packages comprises presentation by the digital processor to the user of a set of icons representing virtual case package files and slides in a virtual carrier and further comprising user manipulation of the icons to make selections and alteration of the icons by the digital processor to reflect progress of review of the images by the user.

32. The method of claim 31, wherein the user manipulation of the icons includes selection of case packages for review and at least one of categorization of case packages, establishing an order for the case packages, temporarily suspending review of a given one of said case packages while retaining information thereon during review of a different one of the case packages, sending and receiving case packages, and signing off on a case package after review.

33. The method of claim 31, wherein manipulation of the icons includes selection of one of case packages and information within case packages for action, and alteration of one of size, shape, position, location and appearance of an icon, by at least one of the user and the digital processor; and the user manipulation of the icons includes selection of case packages for review and at least one of categorization of case packages, establishing an order for the case packages, temporarily suspending review of a case package while retaining information thereon, sending and receiving case packages, and signing off on a case package after review.

34. The method of claim 31, wherein the user review of the case packages comprises, in addition to displaying microscopic images, the user selecting among altering a presentation of at least one icon associated with one of a slide and a case package, annotating one of said images, entering data respecting the image, storing data representing at least one location on the image, processing the image to determine a dimension, altering a display parameter of the image with respect to one of orientation, staged position and magnification, and reverting to a same point in a series of workflow steps, with previously completed steps stored and identified as completed after temporarily departing from an associated case package.

35. The method of claim 23, wherein said presentation and manipulation of the images and the case packages includes representing plural case packages in at least one identified pile from which individual case packages can be selected, and representing plural associated slides as a slide rack from which individual slides can be selected.

36. The method of claim 35, further comprising presenting at least one display for said case packages, containing at least one representation of a slide in the case package shown as a distinct place holder representation, in a case of a slide that has been identified as prospectively expected or a formerly available, but for which at least one form of image is not presently available for viewing.

37. The method of claim 35, comprising representing said plural case packages in piles of which at least certain piles are defined by programming of the digital processor and further comprising assigning the case packages to the piles as a step in a workflow.

38. The method of claim 35, comprising representing the individual slides using icons that are one of highlighted, distinctly colored, distinctly oriented and distinctly located to identify a status that is changed by one of the processor and the user as a case package proceeds through said examination.

39. The method of claim 23, further comprising recording in the database information provided by the user during said examination, wherein the user concludes the examination of case packages by entering data indicating completion.

40. The method of claim 23, further comprising recording in the workflow database a current status of the examination of each said case package under review; suspending review of a given case package under operation by the user of an input to switch to review of a different case package; saving said current status of the given case package; and thereafter switching back to said current status of the given case package to resume the examination where left off.

* * * * *